United States Patent [19]
Tjoeng et al.

[11] Patent Number: 5,792,758
[45] Date of Patent: Aug. 11, 1998

[54] STEROID NITRITE ESTER DERIVATIVES USEFUL AS ANTI-INFLAMMATORY DRUGS

[75] Inventors: Foe S. Tjoeng, Manchester; Mark G. Currie, St. Charles, both of Mo.; Mark E. Zupec, O'Fallon, Ill.

[73] Assignee: G. D. Searle & Co., Chicago, Ill.

[21] Appl. No.: 569,269

[22] Filed: Dec. 8, 1995

[51] Int. Cl.⁶ .............................. C07J 71/00; A61K 31/58
[52] U.S. Cl. .................. 514/173; 514/172; 514/174; 540/4; 540/27; 540/63
[58] Field of Search .................. 540/4, 27, 63; 514/172, 173, 174

[56] References Cited

U.S. PATENT DOCUMENTS

| | | | |
|---|---|---|---|
| 3,215,713 | 11/1965 | Barton | 260/397.4 |
| 3,218,340 | 11/1965 | Tadanier | 260/397.4 |
| 3,298,941 | 1/1967 | Barton | 204/158 |
| 3,494,941 | 2/1970 | Ledig et al. | 260/397.4 |
| 3,639,434 | 2/1972 | Oxley et al. | 260/397.45 |
| 3,674,817 | 7/1972 | Baldratti et al. | 260/397.4 |
| 3,743,741 | 7/1973 | Laurent et al. | 424/242 |
| 3,781,312 | 12/1973 | Phillips et al. | 260/397.45 |
| 3,806,502 | 4/1974 | Megges et al. | 260/210.5 |
| 3,894,004 | 7/1975 | Hofmeister et al. | 260/239.5 |
| 3,930,970 | 1/1976 | Barton | 204/158 R |
| 3,963,707 | 6/1976 | Hogberg et al. | 260/239.55 |
| 3,980,681 | 9/1976 | Sykes et al. | 260/397.45 |
| 4,102,908 | 7/1978 | Hofmeister et al. | 260/397.4 |
| 4,201,778 | 5/1980 | Draper | 424/241 |
| 4,322,349 | 3/1982 | Annen et al. | 260/239.55 |

FOREIGN PATENT DOCUMENTS

| | | |
|---|---|---|
| 969927 | 6/1975 | Canada . |
| 975755 | 10/1975 | Canada . |
| 41337161 | 2/1963 | France . |
| 2222491 | 11/1972 | Germany . |
| 1643034B2 | 1/1976 | Germany . |
| 4223800A1 | 1/1994 | Germany . |
| 1082573 | 9/1967 | United Kingdom . |
| WO9403421-A2 | 2/1994 | WIPO . |
| WO9404484-A1 | 3/1994 | WIPO . |

OTHER PUBLICATIONS

Buckell et al., *J. Chem. Soc. Perkin Trans. 2* (1994), 401–403.
Cederqvist et al., *Biochem. Pharm.*, vol. 47, No. 6 (1994), 1047–1053.
Kowaluk, *Journ. Pharm. and Exper. Therap.*, vol. 259, No. 2 (1991), 519–525.
Moncada et al., *Biochem.Pharm.* 38:1709–1715 (1989).
Moncada et al., *Pharm.Review* 43:109–147 (1991).
Hernandez et al., *Journ.Cardio.Pharm* 17:525 (1991).
Persson et al., *Eur.Journ.Pharm.* 249 R7–R8 (1993).
Alspaugh & Granger, *Infection and Immunity*, 59:2291–2296 (1991).
Wallace et al., *Eur.Jour.Pharm.* 257:249–255 (1994).
MacIntrye et al., *Proc.Nat.Acad.Sci.* USA 88 2936–2940 (1991).
Gilman et al., *Pharm.Basis Therap.* Pergamon Press, 1431–1462 (1990).
Green et al., *J. Labelled Compd. Radiopharm.* 17(6), 911–19, 1980.

*Primary Examiner*—Deborah C. Lambkin
*Assistant Examiner*—Laura L. Stockton
*Attorney, Agent, or Firm*—Dennis A. Bennett; Alan L. Scrivner

[57] ABSTRACT

The present invention discloses novel steroid nitrite ester derivatives, and to their use treating inflammatory diseases.

18 Claims, 1 Drawing Sheet

Effect of Nitrosteroids on Aortic Ring Relaxation

STEROID NITRITE ESTER DERIVATIVES USEFUL AS ANTI-INFLAMMATORY DRUGS

BACKGROUND OF THE INVENTION

1. Field of the Invention

The present invention relates to novel steroid nitrite ester derivatives, and to their use treating inflammatory diseases.

2. Related Art

Steroids, specifically of the glucocorticoid class of molecules, are known to possess anti-inflammatory and immunomodulatory activities and are commonly utilized for the treatment of numerous autoimmune and inflammatory diseases. However, their beneficial effects are often slow to develop and accompanied by many dose-limiting side-effects. Nitric oxide donors, such as nitroglycerin, have also been utilized as pharmaceutical agents with prominent beneficial effects on the cardiovascular system. Many of the biological actions of nitric oxide potentially counteract the side-effects of the glucocorticoids and may enhance their therapeutic actions. The present invention relates to novel steroid nitrite ester derivatives that possess the combined biological properties of glucocorticoids and nitric oxide donors in a single molecule. These molecules have an advantage over currently utilized glucocorticoids in that they rapidly elicit beneficial pharmacological effects, such as bronchial relaxation, through the release of nitric oxide. It is intended that these novel molecules be utilized for therapy, in particular their use as anti-inflammatory and immunosuppressive drugs for the treatment of rheumatic diseases, immunological disorders, skin disorders, inflammation, transplant rejection, cancer, osteoporosis, rhinitis and asthma with lowered side-effects.

Glucocorticoids are commonly utilized for the pharmacologic treatment of inflammation and undesirable immune system reactions. These steroids have the capacity to prevent or suppress the development of inflammation resulting from a number of different injurious agents including infectious, immunological, chemical, mechanical, and radiation. Glucocorticoids are also effective in the treatment of immune system disorders including autoimmune diseases such as rheumatoid arthritis and lupus, and transplant rejection. However, the therapeutic applications of these steroids are somewhat limited due to toxicity and side-effects. The major side effects of the glucocorticoids are hypertension, peptic ulcers, increased susceptibility to infections, osteoporosis, hyperglycemia, and vascular occlusion.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite ester, glyceryltrinitrate and other nitrovasodilators. The recent identification of EDRF as NO has coincided with the discovery of a biochemical pathway by which NO is synthesized from the amino acid L-arginine by the enzyme nitric oxide synthase. The NO released by the constitutive enzyme acts as a transduction mechanism underlying several physiological responses. The NO produced by the inducible enzyme is a cytotoxic molecule for tumor cells and invading microorganisms.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al Biochemical Pharmacology, 38, 1709–1715 (1989) and Moncada et al. Pharmacological Reviews, 43, 109–142 (1991). Furthermore, NO has been shown to possess anti-thrombotic (see Moncada et al. Journal of Cardiovascular Pharmacology 17, S25 (1991), Byrne et al., World Patent application WO9403421-A2 and Schonafinger et al., German Patent application DE4223800-A1), bronchorelaxant (Persson et al. European Journal of Pharmacology, 249, R7–R8 (1993), anti inflammatory, microbialcidal (Alspaugh and Granger, Infection and Immunity 59, 2291–2296 (1991) and gastroprotective (see Wallace et al. European Journal of Pharmacology, 257, 249–255 (1994) effects in animal models. In addition, nitric oxide has been suggested to be effective against the loss of bone in in vitro models of osteoporosis (MacIntyre et al. Proc.Natl.Acad.Sci.USA 88, 2936–2940 (1991) and in inhibiting angiogenesis, tumour growth and metastasis in in vivo animal models (PipiliSynetos et al. British Journal of Pharmacology, 116, 1829–1834 (1995). In U.S. Pat. Nos. 3,930,970, 3,298,941 and 3,215,713, a novel photochemical process for the preparation of diol mononitrates from alcohol nitrites is disclosed. In U.S. Pat. Nos. 3,639,434, 3,743,741 and 3,839,369, the preparation of steroid nitrate esters and their uses as intermediates is disclosed. In German Patent 1643034, a method for the preparation of steroid nitrate esters is disclosed. In Canadian Patent 975755 and 969927, a process for the preparation and acidolysis of nitrate esters of 21-alcohols of the pregnane series is disclosed, respectively. In British Patent 1,082,573 and 1,082,574, a process for the preparation of steroid-11-nitrate esters and their uses as intermediates is disclosed Thus, these properties make nitric oxide an ideal agent to enhance the actions of corticosteroids in the treatment of various diseases mentioned earlier by both increasing their biological effects as well as by reducing their side effects. The present invention relates to novel nitrite ester esters of steroids, processes for their preparation, pharmaceutical compositions containing them, and methods for their use.

SUMMARY OF THE INVENTION

The present invention discloses steroid nitrite ester derivatives of the Formula I.

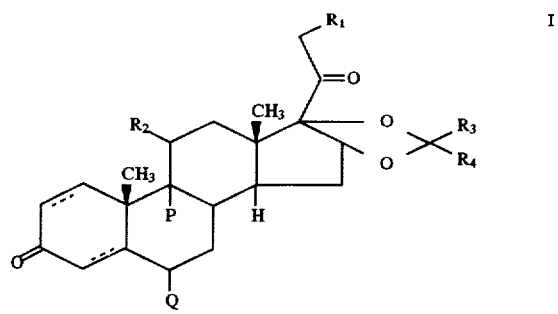

and pharmaceutically acceptable ester and prodrugs thereof, wherein;

the dotted line indicates a single or a double bond;

$R_1$ is selected from the group consisting of hydrogen, hydroxy, nitrite ester (ONO), nitrate ester (ONO$_2$), halogen, sulfhydryl, lower thioalkyl, acyloxy, lower alkoxy, alkylsilyloxy, lower alkyl, lower alkenyl, lower alkynyl, alicyclic hydrocarbon and heterocyclic;

$R_2$ is selected from the group consisting of hydrogen, hydroxy, nitrite ester (ONO), nitrate ester (ONO$_2$), and acyloxy;

$R_3$ and $R_4$ are independently selected from the group consisting of hydrogen, lower alkyl, alicyclic hydrocarbon, heterocyclic hydrocarbon, lower alkenyl and lower alkynyl;

optionally $R_3$ and $R_4$ can form an alicyclic hydrocarbon or heterocyclic group;

P and Q are independently selected from the group consisting of hydrogen, halogen, lower alkyl, lower alkenyl, and lower alkynyl; and With the proviso that $R_1$ or $R_2$ or $R_1$ and $R_2$ are nitrite ester (ONO).

The invention further relates to pharmaceutical compositions comprising a compound of formula I. The compounds and pharmaceutical compositions defined above have usefulness as anti inflammatory and immunosuppressive drugs for treatment of rheumatic diseases, immunological disorders, skin disorders, inflammation, transplant rejection, osteoporosis, cancer, rhinitis and asthma. These compounds combine the previously described actions of the steroids and NO in a single molecule. The novel compounds of the present invention may exert their steroid activities directly with the NO still attached or after the NO is released, whereby the compound is converted back to its parent steroid.

DETAILED DESCRIPTION OF THE INVENTION

Figure 1:
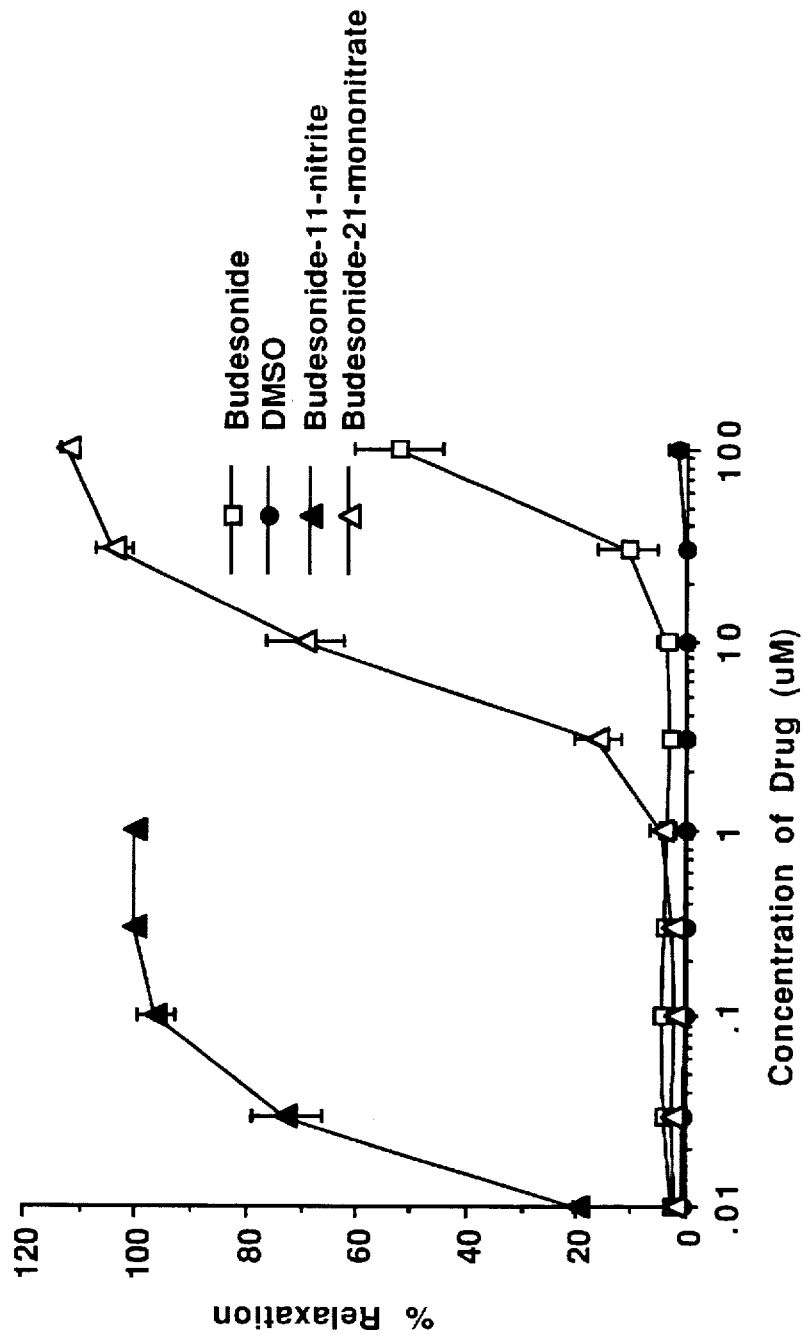
FIG. 1 shows the effect on Aortic Ring Relaxation of the title compound in Example 1.

A preferred embodiment of the present invention is a compound of the formula (I)

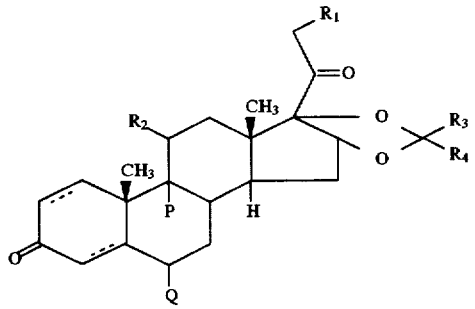

wherein;

the dotted lines indicate a single or a double bond;

$R_1$ is selected from the group consisting of nitrite ester (ONO), nitrate ester ($ONO_2$), halogen, sulfhydryl, lower thioalkyl group of 1 to 4 carbon atoms, acyloxy group of 2 to 6 carbon atoms, lower alkoxy group of 1 to 6 carbon atoms, alkylsilyloxy group of 3 to 8 carbon atoms, lower alkyl group of 1 to 6 carbon atoms, heterocyclic group of 2 to 5 carbon atoms and 1 to 2 hetero atoms, and alicyclic hydrocarbon group of 3 to 6 carbon atoms;

$R_2$ is selected from the group consisting of hydrogen, hydroxy, nitrite ester (ONO), nitrate ester ($ONO_2$), and acyloxy group of 2 to 4 carbon atoms;

$R_3$ and $R_4$ are independently selected from the group consisting of hydrogen, lower alkyl of 1 to 8 carbon atoms, alicyclic of 3 to 8 carbon atoms, and heterocyclic of 2 to 5 carbon atoms and 1 to 2 heteroatoms;

optionally $R_3$ and $R_4$ can form an alicyclic of 3 to 8 carbon atoms or heterocyclic group of 3 to 6 carbon atoms and 1 to 2 hetero atoms;

P and Q are independently selected from the group consisting of hydrogen, chloro, fluoro and lower alkyl group of 1 to 4 carbon atoms; and With the proviso that $R_1$ or $R_2$ or $R_1$ and $R_2$ are nitrite ester (ONO).

Another preferred embodiment of the present invention is a compound of the formula I:

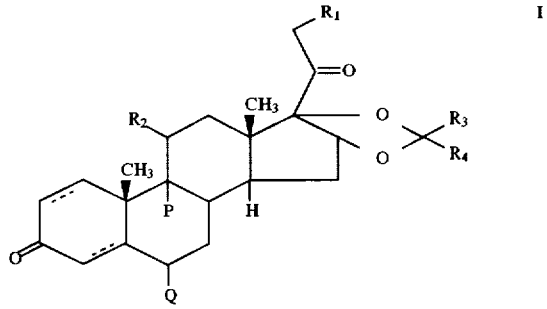

wherein the dotted lines indicate a single or a double bond;

$R_1$ is selected from the group consisting of hydrogen, hydroxy, nitrite ester (ONO), nitrate ester ($ONO_2$), halogen, sulfhydryl, lower thioalkyl group of 1 to 4 carbon atoms, heterocyclic group of 2 to 4 carbon atoms and 1 to 2 hetero atoms, lower alkoxy group of 1 to 4 carbon atoms, alkylsilyloxy group of 3 to 6 carbon atoms, lower alkyl group of 1 to 4 carbon atoms, and acyloxy group of 2 to 4 carbon atoms;

$R_2$ is selected from the group consisting of hydroxy, nitrite ester (ONO), nitrate ester ($ONO_2$), and acyloxy group of 2 to 3 carbon atoms;

$R_3$ and $R_4$ are independently selected from the group consisting of hydrogen, and lower alkyl group of 1 to 6 carbon atoms;

optionally $R_3$ and $R_4$ can form an alicyclic hydrocarbon of 3 to 6 carbon atoms or heterocyclic group of 2 to 4 carbon atoms and 1 to 2 hetero atoms;

P and Q are independently selected from group consisting of hydrogen, chloro, fluoro and lower alkyl group of 1 to 3 carbon atoms; and With the proviso that $R_1$ or $R_2$ or $R_1$ and $R_2$ are nitrite ester (ONO).

Another preferred embodiment of the present invention is a compound of the formula I:

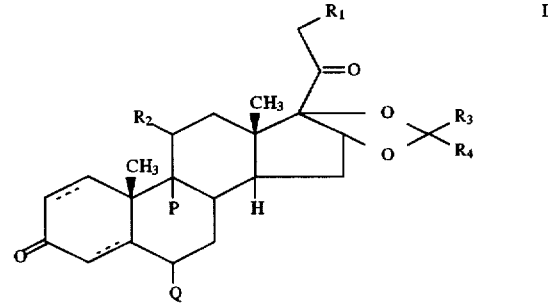

wherein;

the dotted lines indicates a single or a double bond;

$R_1$ is selected from the group consisting of hydroxy, nitrite ester (ONO), nitrate ester ($ONO_2$), and chloro;

$R_2$ is selected from the group consisting of hydroxy, nitrite ester (ONO), and nitrate ester ($ONO_2$);

$R_3$ and $R_4$ are independently selected from the group consisting of hydrogen, methyl, ethyl and propyl;

P and Q are independently selected from a group of hydrogen, chloro, fluoro and methyl;

With the proviso that at $R_1$ or $R_2$ is nitrite ester (ONO).

While it may be possible for the preparations or compounds as defined above to be administered as the raw chemical, it is preferable to present them as a pharmaceutical formulation. According to a further aspect, the present invention provides a pharmaceutical formulation comprising a preparation or a compound as defined above or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a preparation or a compound as defined above or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for administration by inhalation can be prepared for use as an aerosolized medicaments such as in manner recited in U.S. Pat. No. 5,458,135 and U.S. Pat. No. 5,447,150.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally, via inhalation or via injection at a dose of from 0.01 to 500 mg/kg per day. The dose range for adult humans is generally from 0.1 mg to 1 g/day. Tablets or other forms of presentation provided in discrete units may conveniently contain an amount of compound of the invention which is effective at such dosage or as a multiple of the same, for instance, units containing 0.05 mg to 250 mg, usually around 0.1 mg to 100 mg.

The compounds of formula (I) are preferably administered orally or as an aerosolized medicament. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, isoamyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" means an aliphatic hydrocarbon radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "acyloxy" means alkanoyl radical with 2 to about 5 carbon atoms. Suitable examples include acetyloxy, propanoyloxy, butanoyloxy, benzoyloxy and the like.

The term "heterocyclic" means a saturated or unsaturated cyclic hydrocarbon radical with 2 to about 6 carbon atoms, preferably about 3 to about 5; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo (b) thiophenyl, benzimidazolyl, quinolinyl, and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, isobutoxy, sec-butoxy, tert-butoxy and the like.

The term "lower thioalkyl" means the same as "alkoxyl" except sulfur replaces oxygen.

The term "alkylsilyloxy" means alkylsilyl other radical wherein the term alkyl is as defined above and most preferably containing 3 to 8 carbon atoms. Examples of suitable alkylsilyl ether radicals include trimethylsilyl, t-butyldimethylsilyl and the like.

The term "halogen" means fluorine, chlorine, bromine or iodine.

The term "haloalkyl" means a lower alkyl as defined above having 1–5 preferably 1–3 halogens attached to said lower alkyl chain.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

Starting materials used to make the present invention are commercially available such as from Aldrich, Fluka or Sigma Chemical Company.

Three general synthetic schemes are outlined below for the compounds of the present invention:

SCHEME I

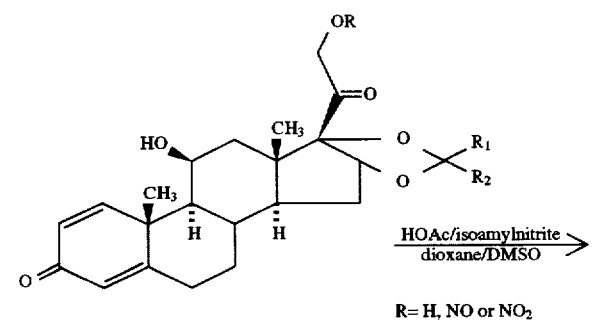

HOAc/isoamylnitrite
dioxane/DMSO

R= H, NO or NO₂

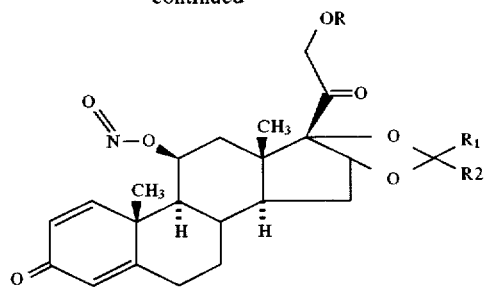

SCHEME II

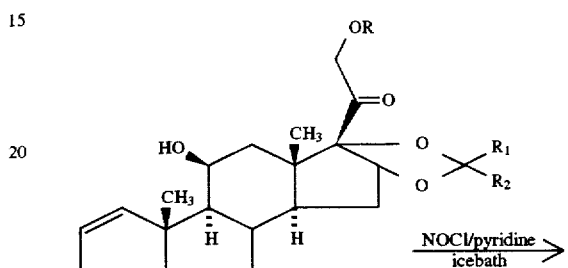

NOCl/pyridine
icebath

R= H, NO or NO₂

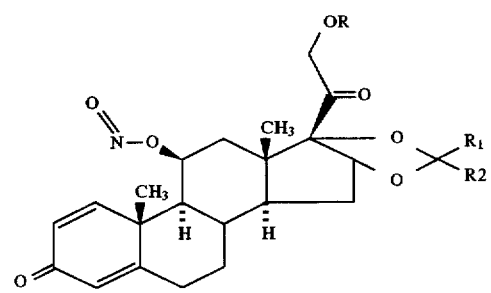

SCHEME III

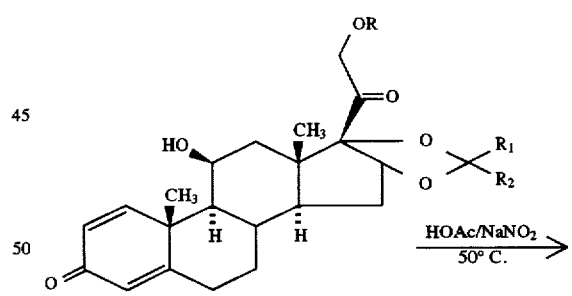

HOAc/NaNO₂
50° C.

R= H, NO or NO₂

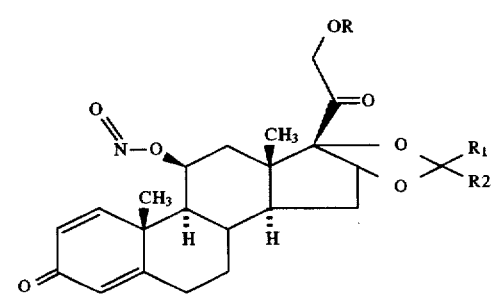

It will be obvious to one skilled in the art to make modifications in the choice of starting materials and process conditions to make all of the invention compounds disclosed herein.

The present invention is illustrated by the following examples:

EXAMPLE 1

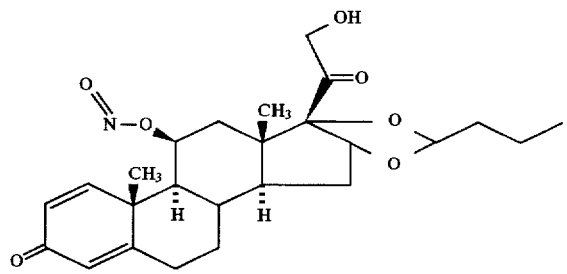

A solution of budesonide (0.11 g; 0.26 mmoles) in acetic acid (5 ml) was warmed up to 55° C. and treated with solid sodium nitrite ester (0.072 g; 1 mmole) for 30 seconds. The product was precipitated by addition of ice water (25 ml) and filtered. The solid was washed with water and dried over $P_2O_5$ in vacuo to give a white solid material. FAB-MS: $(M+Li)^+=466$; $^1$H-NMR ($CDCl_3$) d 0.91 (s,3H,$CH_3$(C-18)), 1.45 (s,3H,$CH_3$(C-19)), 4.5 (m,2H, CO—$CH_2$—O), 5.2 (m,1H, CH(C-22)), 6.06 (s,1H,CH(C-4)), 6.2 (s,1H,CH(C-11)), 6.3 (d,1H,CH(C-2)), 6.83 (d,1H,CH(C-1)).

EXAMPLE 2

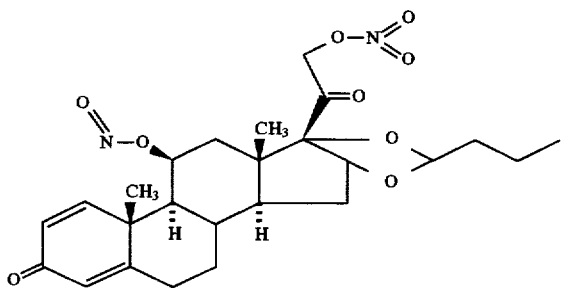

A. Preparation of Budesonide-21-Nitrate ester: Fuming nitric acid (0.5 ml; d=1.49) and acetic anhydride (2 ml) were combined at −10° C. To this solution, a pre-cooled suspension of 16a,17-butylidenedioxyprednisolone (1 g; 2.3 mmoles) in chloroform (10 ml) was added dropwise with stirring. The progress of the reaction was monitored by TLC and HPLC. The mixture was stirred for another hour in an ice bath and poured into ice water (50 ml). The organic phase was separated and washed with water, saturated sodium bicarbonate solution and water. After drying over sodium sulfate overnight, the solid was filtered and the filtrate was taken down to dryness. The residue was purified on a Waters μBondapak column (1.9 cm×15 cm) using a linear gradient of 25–75% acetonitrile/water/ trifluoro-acetic acid. The desired fractions were collected and lyophilized to give 800 mg of white material. FAB-MS: $(M+Li)^+=482.5$; $^1$H-NMR ($CDCl_3$) d1.45 (s,3H,$CH_3$(C-19)), 4.51–4.57 (m,1H,CH(C-11)), 4.62 (t,1H,CH(C-21)), 4.86 (d,1H,CH(C-16)), 5.13 (t,1H,CH(C-21)), 5.18 (m,1H,CH(C-22)), 6.04 (s,1H,CH(C-4)), 6.38 (d,1H,CH(C-2)), 7.24 (d,1H,CH(C-1)).

B. A solution of budesonide-21-nitrate ester (0.01 g; 0.02 mmoles) in acetic acid (1 ml) was warmed up to 55° C. and treated with solid sodium nitrite ester (0.007 g; 0.1 mmole) for 30 seconds. The product was precipitated by addition of ice water (5 ml) and filtered. The solid was washed with water and dried over $P_2O_5$ in vacuo to give a white solid material. FAB-MS: $(M+Li)^+=511$. $^1$H-NMR ($CDCl_3$) d 0.95 (s,3H,$CH_3$(C-25)), 1.2 (s,3H,$CH_3$(C-18)), 1.6 (s,3H,$CH_3$(C-19)), 4.63 (t,1H,CH(C-21)), 4.83 (d,1H,CH(C-16)), 5.09 (t,1H,CH(C-21)), 5.16 (t,1H,CH(C-22)), 6.2 (m,1H,CH(C-11)), 6.09 (s,1H,CH(C-4)), 6.35 (d,1H,CH(C-2)), 6.88 (d,1H,CH(C-1)).

EXAMPLE 3

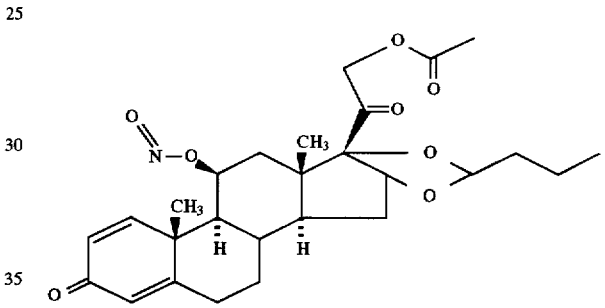

Budesonide-11-nitrite ester (0.23 g; 0.5 mmoles) in chloroform/pyridine (10 ml; 1:1) is treated with acetic anhydride (5 ml) with stirring at room temperature. The reaction is monitored by HPLC and carried out until completion. The crude product is purified by reversed-phase HPLC to generate the title compound.

EXAMPLE 4

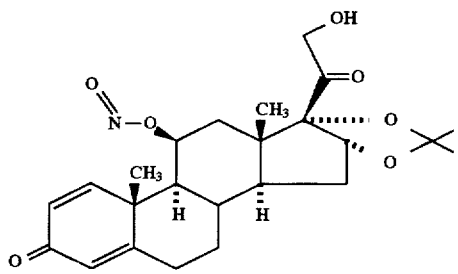

The title compound is prepared from desonide and sodium nitrite ester in acetic acid by the method of EXAMPLE 1.

EXAMPLE 5

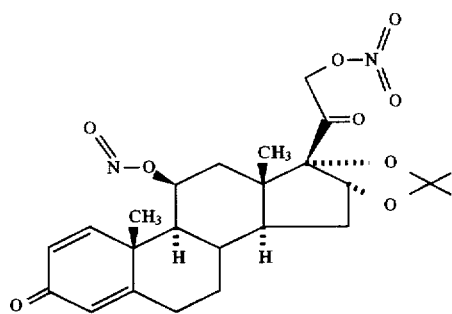

A. Preparation of desonide-21-nitrate ester: The compound was prepared from the 16a, 17a-isopropylidenedioxyprednisolone (1 g; 2.4 mmoles) in the same manner as described for EXAMPLE 2. FAB-MS: $(M+Li)^+=468.3$; $^1$H-NMR (CDCl$_3$) d 0.94 (s,3H,CH$_3$(C-18)), 1.44 (s,3H,CH$_3$ (C-19)), 4.53–4.55 (m,1H,CH(C-11)), 5.00 (d,1H,CH(C-16)), 5.03 (d,1H,CH(C-21)), 5.37 (d,1H,CH(C-21)), 6.04 (s,1H,CH(C-4)), 6.30 (d,1H,CH(C-2)), 7.24 (d,1H,CH(C-1)).

B. Desonide-21-nitrate ester from above preparation is reacted with sodium nitrite ester in acetic acid by the method of EXAMPLE 1 to produce the title compound

EXAMPLE 6

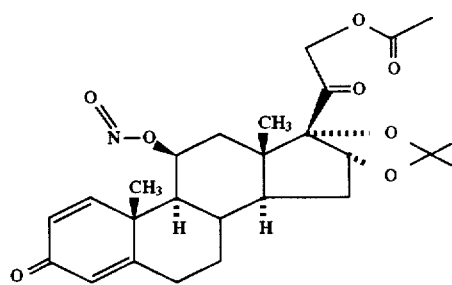

The product of EXAMPLE 4 is treated with acetic anhydride in pyridine/chloroform by the method of EXAMPLE 3 to give the title product.

EXAMPLE 7

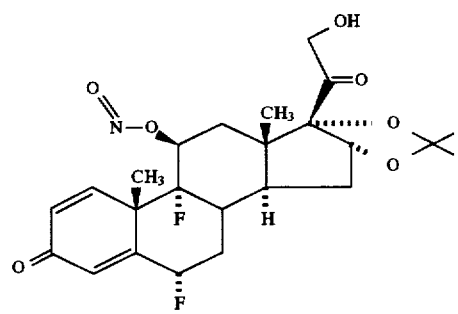

Fluocinolone is reacted with sodium nitrite ester/acetic acid by the method of EXAMPLE 1 to generate the title compound.

EXAMPLE 8

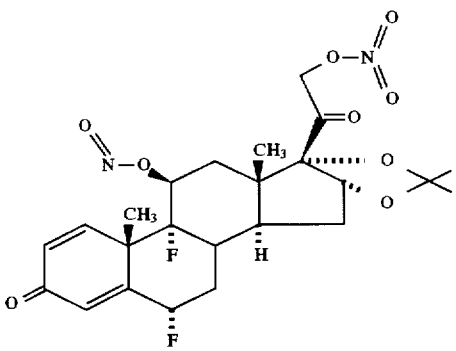

A. Preparation of fluocinolone-21-nitrate ester: The compound is prepared from 6a,9a-difluoro-16a-hydroxyprednisolone-16,17-acetonide (1 g; 2.2 mmoles) in the same manner as described for EXAMPLE 2. FAB-MS: $(M+Li)^+=504.2$; $^1$H-NMR (CDCl$_3$) d 0.93 (s,3H,CH$_3$(C-18)), 1.54 (s,3H,CH$_3$(C-19)), 4.42–4.48 (m,1H,CH(C-11)), 5.03 (d,1H,CH(C-16)), 5.05 (d,1H,CH (C-21)), 5.37 (d,1H,CH(C-21), 6.39 (d,1H,CH(C-2)), 6.44 (s,1H,CH(C-4)), 7.14 (d,1H,CH(C-1)).

B. Fluocinolone-21-nitrate ester from above preparation is reacted with sodium nitrite ester in acetic acid by the method of EXAMPLE 1 to produce the title compound.

EXAMPLE 9

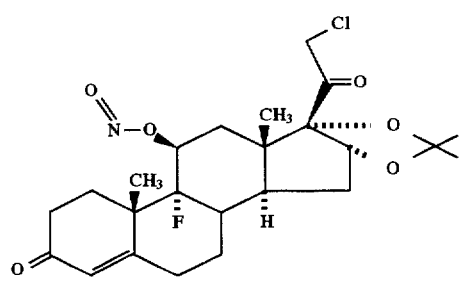

The product of EXAMPLE 7 is treated with acetic anhydride in pyridine/chloroform by the method of EXAMPLE 3 to give the title product.

EXAMPLE 10

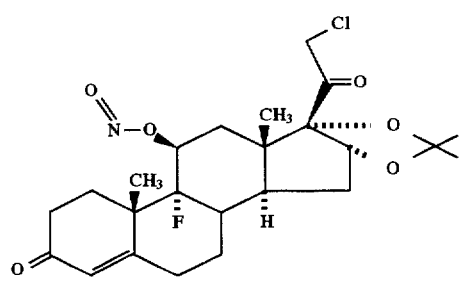

Halcinonide is reacted with sodium nitrite ester/acetic acid by the method of EXAMPLE 1 to generate the title compound.

EXAMPLE 11

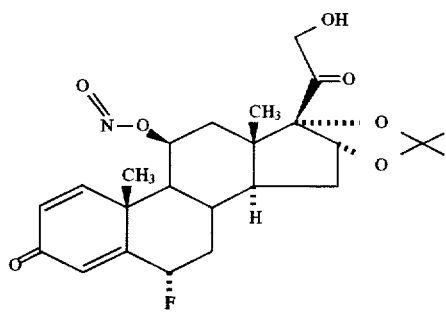

Flunisolide is reacted with sodium nitrite ester/acetic acid by the method of EXAMPLE 1 to generate the title compound.

EXAMPLE 12

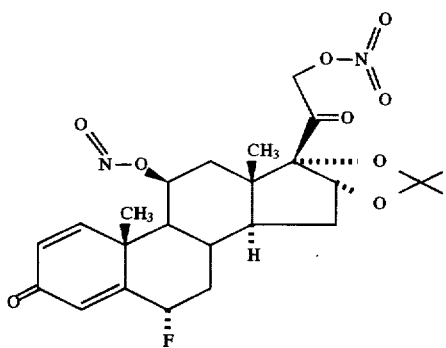

A. Preparation of Fluonisolide-21-nitrate ester: The compound is prepared from 6a-fluoro-16a,17-isopropylidenedioxy-prednisolone (1 g; 2.3 mmoles) in the same manner as described for EXAMPLE 2. FAB-MS: $(M+Li)^+=486.3$; $^1H$-NMR $(CDCl_3)$ d 0.94 (s,3H,CH$_3$(C-18)), 1.44 (d,3H,CH$_3$(C-19)), 4.53–4.57 (m,1H,CH(C-11)), 5.01 (d,1H,CH(C-16)), 5.04 (d,1H,CH(C-21)), 5.36 (d,1H,CH(C-21)), 6.34 (s,1H,CH(C-4)), 7.17 (d,1H,CH(C-2)), 7.26 (s,1H,CH(C-1)).

B. Fluonisolide-21-nitrate ester from above preparation is reacted with sodium nitrite ester/acetic acid by the method of EXAMPLE 1 to generate the title compound.

EXAMPLE 13

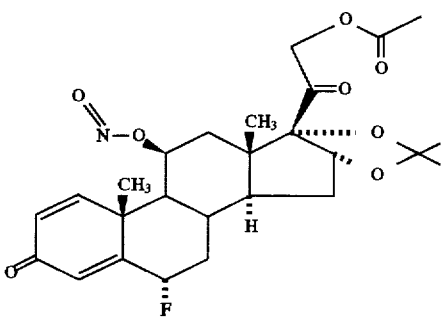

The product of EXAMPLE 11 is treated with acetic anhydride in pyridine/chloroform by the method of EXAMPLE 3 to give the title product.

EXAMPLE 14

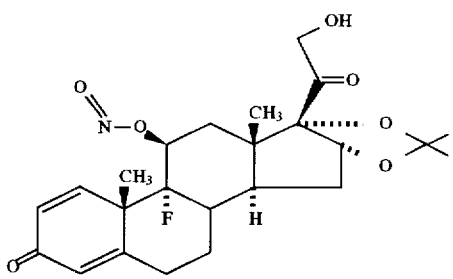

Triamcinolone acetonide is reacted with sodium nitrite ester/acetic acid by the method of EXAMPLE 1 to generate the title compound.

EXAMPLE 15

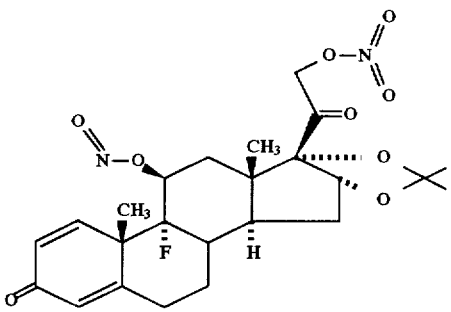

A. Preparation of triamcinolone acetonide-21-nitrate ester The compound is prepared from 9a-fluoro-16a,17-isopropylidenedioxy-prednisolone in the same manner as described for EXAMPLE 2.

B. Triamcinolone acetonide-21-nitrate ester from above preparation is reacted with sodium nitrite ester/acetic acid by the method of EXAMPLE 1 to generate the title compound.

EXAMPLE 16

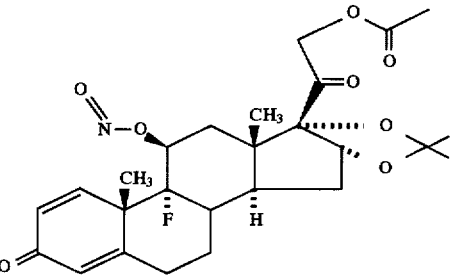

The product of EXAMPLE 14 is treated with acetic anhydride in pyridine/chloroform by the method of EXAMPLE 3 to give the title product.

EXAMPLE 17

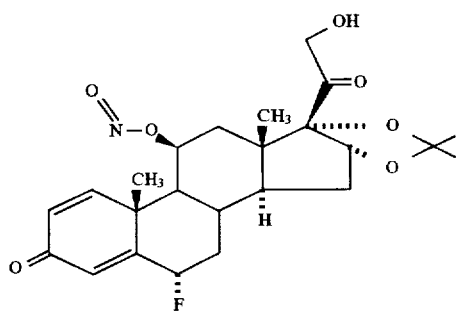

Flurandrenolide is reacted with sodium nitrite ester/acetic acid by the method of EXAMPLE 1 to generate the title compound.

EXAMPLE 18

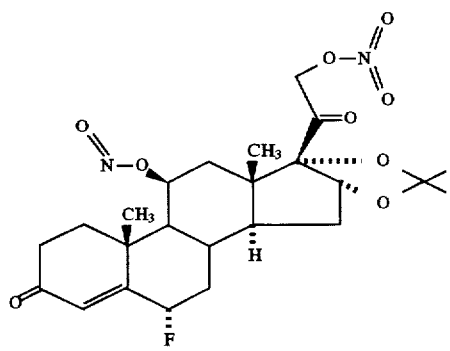

A. Preparation of flurandrenolide-21-nitrate ester The compound is prepared from 9a-fluoro-16a,17-isopropylidenedioxy-prednisolone in the same manner as described for EXAMPLE 2.

B. Flurandrenolide-21-nitrate ester from above preparation is reacted with sodium nitrite ester/acetic acid by the method of EXAMPLE 1 to generate the title compound.

EXAMPLE 19

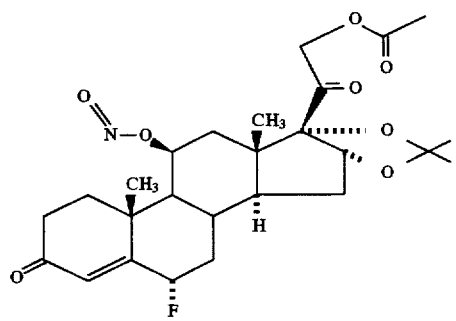

The product of EXAMPLE 17 is treated with acetic anhydride in pyridine/chloroform by the method of EXAMPLE 3 to give the title product.

EXAMPLE 20

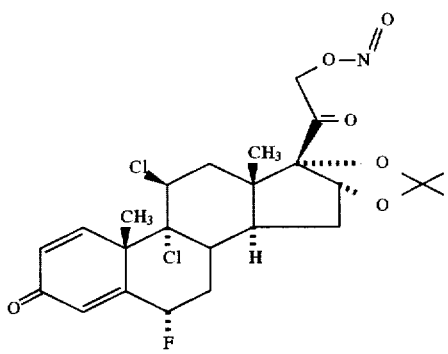

Flucloronide is reacted with sodium nitrite ester/acetic acid by the method of EXAMPLE 1 to generate the title compound.

EXAMPLE 21

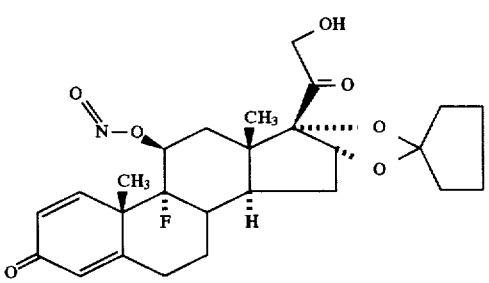

9a-fluoro-16,17-cyclopentylidenebis(oxy)-11,21-dihydroxypregna-1,4diene-3,20-dione is reacted with sodium nitrite ester/acetic acid by the method of EXAMPLE 1 to generate the title compound.

EXAMPLE 22

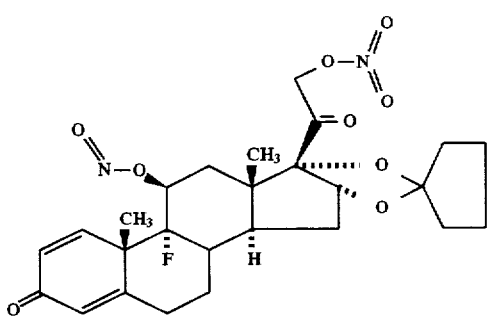

A. Preparation of 9a-fluoro-16,17-cyclopentylidenebis(oxy)-11-hydroxypregna-1,4-diene-3,20-dione-21-nitrate ester: The compound is prepared from 9a-fluoro-16,17-cyclopentylidenebis(oxy)-11,21-dihydroxypregna-1,4-diene-3,20-dione in the same manner as described for EXAMPLE 2.

B. 9a-fluoro-16,17-cyclopentylidenebis(oxy)-11-hydroxypregna-1,4-diene-3,20-dione-21-nitrate ester from above preparation is reacted with sodium nitrite ester/acetic acid by the method of EXAMPLE 1 to generate the title compound.

EXAMPLE 23

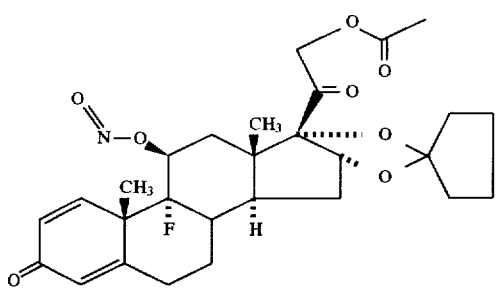

Amcinonide is reacted with sodium nitrite ester/acetic acid by the method of EXAMPLE 1 to generate the title compound.

Biological Data

The subject compounds of the formula (I) have been found to be nitric oxide donors while maintaining their steroid activities and possess useful pharmacological properties as demonstrated by EXAMPLE 1 in the in vitro smooth relaxant activity assay: The test compound and the parent steroid were examined for the ability to relax smooth muscle. The rat aortic ring assay was utilized as a bioassay to measure the relaxant activity. The rings were precontracted with phenylephrine (0.3 uM) and subsequently compounds were added to the tissue bath in the presence of cysteine (Cys) and $N^G$-L-nitroarginine methyl ester (L-NAME):

In vitro smooth muscle relaxant activity assay in the presence of Cys and L-NAME:

| Compound | Relaxation, $EC_{50}$ [µM] |
|---|---|
| budesonide | 100 |
| Example 2A | 5 |
| Example 1 | 0.02 |

These data indicate that these compounds have smooth muscle relaxant activity, while the control compound budesonide did not show any effect.

What is claimed is:

1. A compound having the formula:

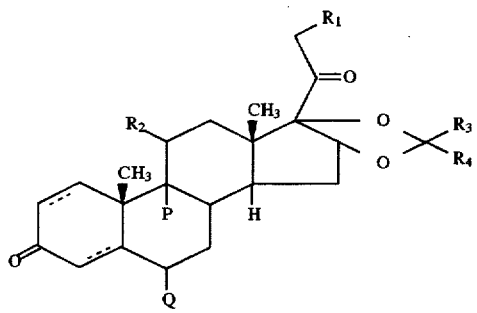

wherein;

the dotted lines indicate a single or a double bond;

$R_1$ is selected from the group consisting of hydroxy, nitrite ester (ONO), nitrate ester ($ONO_2$), and chloro;

$R_2$ is selected from the group consisting of hydroxy, nitrite ester (ONO), and nitrate ester ($ONO_2$);

$R_3$ and $R_4$ are independently selected from the group consisting of hydrogen, methyl, ethyl and propyl;

P and Q are independently selected from a group of hydrogen, chloro, fluoro and methyl; and With the proviso that $R_1$ or $R_2$ or $R_1$ and $R_2$ are nitrite ester (ONO).

2. The compound as recited in claim 1 selected from the group consisting of:

COMPOUND 1

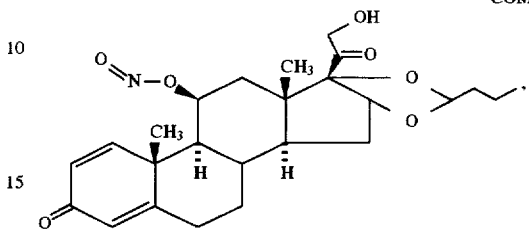

COMPOUND 2

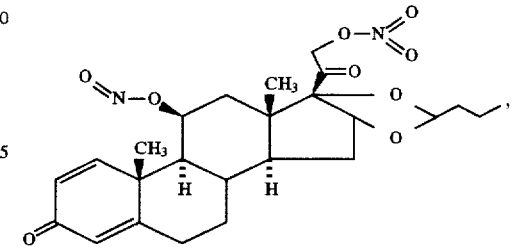

COMPOUND 4

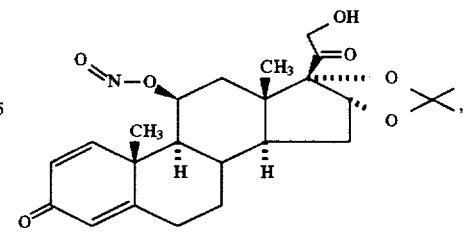

COMPOUND 5

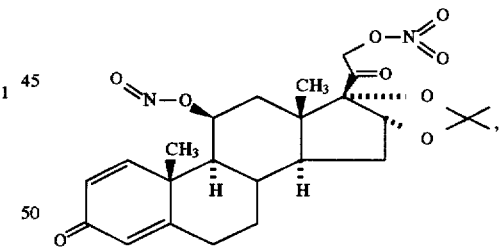

COMPOUND 7

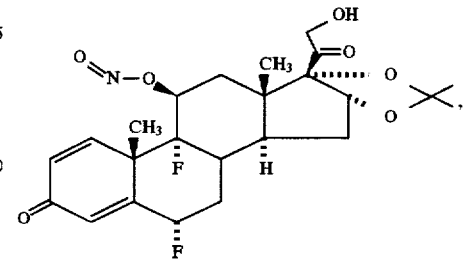

COMPOUND 8
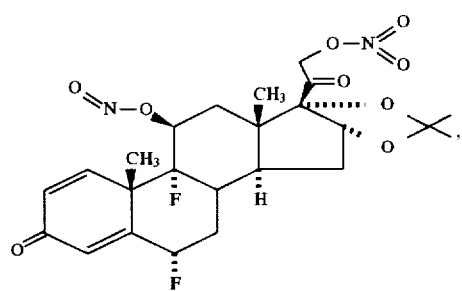

COMPOUND 10
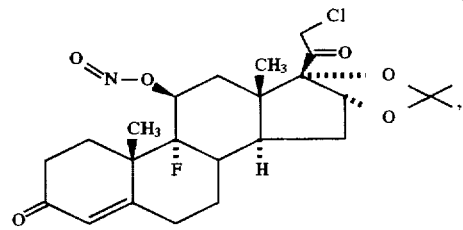

COMPOUND 11
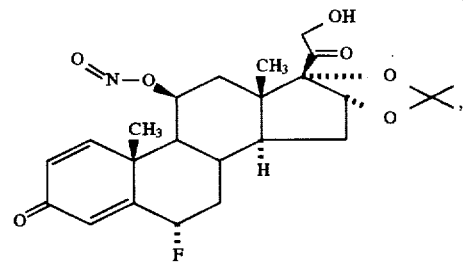

COMPOUND 12
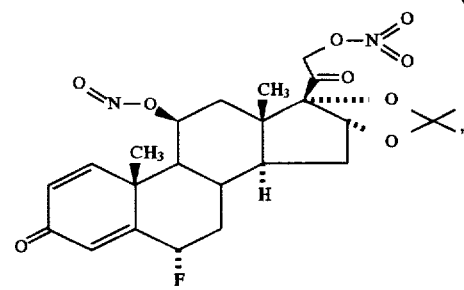

COMPOUND 14
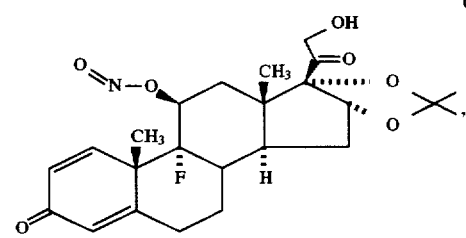

COMPOUND 15
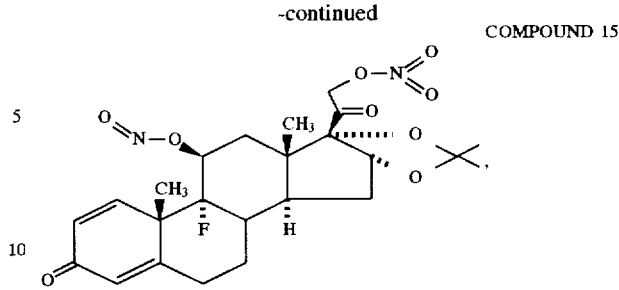

COMPOUND 17
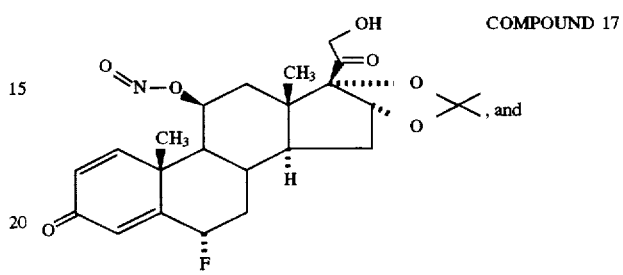, and

COMPOUND 18
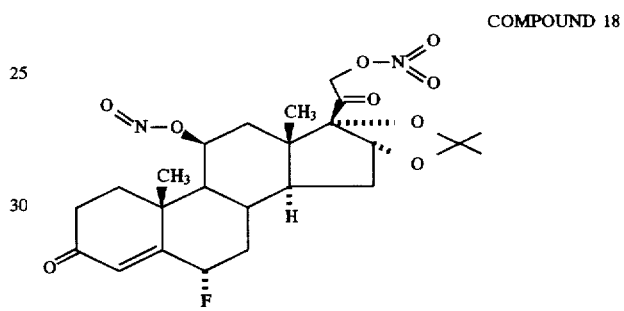

3. A pharmaceutical composition comprising a compound having the formula:

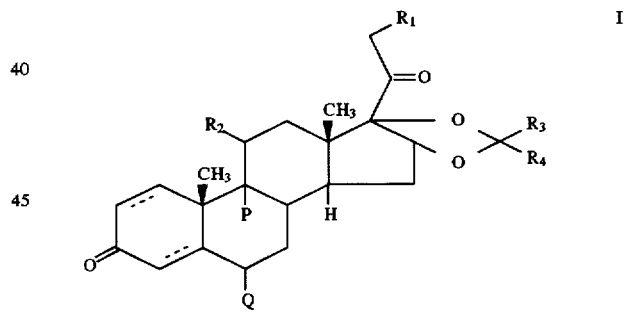

or an ester thereof, wherein;

the dotted line indicates a single or a double bond;

$R_1$ is selected from the group consisting of hydrogen, hydroxy, nitrite ester (ONO), nitrate ester (ONO$_2$), halogen, sulfhydryl, lower thioalkyl, acyloy, lower alkoxy, alkylsilyloxy, lower alkyl, lower alkenyl, lower alkynyl, alicyclic hydrocarbon and heterocyclic;

$R_2$ is selected from the group consisting of hydrogen, hydroxy, nitrite ester (ONO), nitrate ester (ONO$_2$), and acyloxy;

$R_3$ and $R_4$ are independently selected from the group consisting of hydrogen, lower alkyl, lower alkenyl, and lower alkynyl, alicyclic hydrocarbon and heterocyclic;

or $R_3$ and $R_4$ are taken together to form an alicyclic hydrocarbon or heterocyclic ring;

P and Q are independently selected from the group consisting of hydrogen, halogen, lower alkyl, lower alkenyl, and lower alkynyl;

With the proviso that $R_1$ or $R_2$ or $R_1$ and $R_2$ are nitrite ester (ONO); and With the additional proviso that desonide 21-acetate and triamcinolone acetonide 21-acetate are excluded;

together with a pharmaceutically acceptable carrier.

4. The pharmaceutical composition as recited in claim 3 wherein;

the dotted lines indicate a single or a double bond;

$R_1$ is selected from the group consisting of hydrogen, hydroxy, nitrite ester (ONO), nitrate ester ($ONO_2$), halogen, lower thioalkyl group of 1 to 4 carbon atoms, heterocyclic group of 2 to 5 carbon atoms and 1 to 2 hetero atoms, lower alkoxy group of 1 to 6 carbon atoms, alkylcilyloxy group of 3 to 8 carbon atoms, lower alkyl group of 1 to 6 carbon atoms, acyloxy group of 2 to 6 carbon atoms and alicyclic hydrocarbon of 3 to 6 carbon atoms;

$R_2$ is selected from the group consisting of hydrogen, hydroxy, nitrite ester (ONO), nitrate ester ($ONO_2$), and acyloxy group of 2 to 4 carbon atoms;

$R_3$ and $R_4$ are independently selected from the group consisting of hydrogen, lower alkyl of 1 to 8 carbon atoms, alicyclic hydrocarbon of 3 to 6 carbon atoms, and heterocyclic of 2 to 5 carbon atoms and 1 to 2 heteroatoms;

or $R_3$ and $R_4$ are taken together to form an alicyclic of 3 to 8 carbon atoms or heterocyclic ring of 2 to 5 carbon atoms and 1 to 2 hetero atoms;

P and Q are independently selected from the group consisting of hydrogen, chloro, fluoro and lower alkyl group of 1 to 4 carbon atoms;

With the proviso that $R_1$ or $R_2$ or $R_1$ and $R_2$ are nitrite ester (ONO); and With the additional proviso that desonide 21-acetate and triamcinolone acetonide 21-acetate are excluded;

together with a pharmaceutically acceptable carrier.

5. The pharmaceutical composition as recited in claim 3 wherein;

the dotted lines indicate a single or a double bond;

$R_1$ is selected from the group consisting of hydrogen, hydroxy, nitrits ester (ONO), nitrate ester ($ONO_2$), halogen, sulfhydryl, lower thioalkyl group of 1 to 4 carbon atoms, heterocyclic group of 2 to 4 carbon atoms and 1 to 2 hetero atoms, lower alkoxy group of 1 to 4 carbon atoms, alkylsilyloxy group of 3 to 4 carbon atoms, lower alkyl group of 3 to 6 carbon atoms, and acyloxy group of 2 to 4 carbon atoms, $R_2$ is selected from the group consisting of hydroxy, nitrite ester (ONO), nitrate ester ($ONO_2$), and acyloxy group of 2 to 3 carbon atoms;

$R_3$ and $R_4$ are independently selected from the group consisting of hydrogen, and lower alkyl group of 1 to 6 carbon atoms;

or $R_3$ and $R_4$ are taken together to form an alicyclic of 3 to 6 carbon atoms or heterocyclic ring of 3 to 4 carbon atoms and 1 to 2 hetero atoms;

P and Q are independently selected from the group consisting of hydrogen, chloro, fluoro and lower alkyl group of 1 to 3 carbon atoms;

With the proviso that at least one or both $R_1$ or $R_2$ is nitrite ester (ONO); and With the additional proviso that desonide 21-acetate and triamcinolone acetonide 21-acetate are excluded;

together with a pharmaceutically acceptable carrier.

6. The pharmaceutical composition as recited in claim 3 wherein;

the dotted lines indicate a single or a double bond;

$R_1$ is selected from the group consisting of hydroxy, nitrite ester (ONO), nitrate ester ($ONO_2$), and chloro;

$R_2$ is selected from the group consisting of hydroxy, nitrite ester (ONO), and nitrate ester ($ONO_2$);

$R_3$ and $R_4$ are independently selected from the group consisting of hydrogen, methyl, ethyl and propyl;

P and Q are independently selected from a group of hydrogen, chloro, fluoro and methyl; and With the proviso that $R_1$ or $R_2$ or $R_1$ and $R_2$ are nitrite ester (ONO);

together with a pharmaceutically acceptable carrier.

7. The pharmaceutical composition recited in claim 3 wherein the compound is selected from the following:

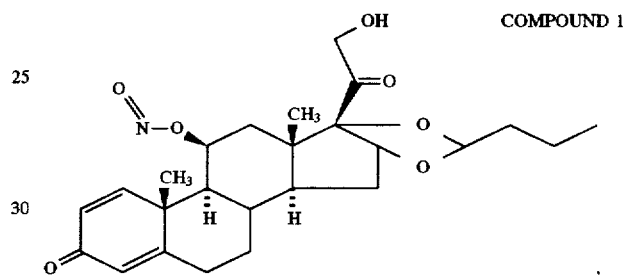

COMPOUND 1

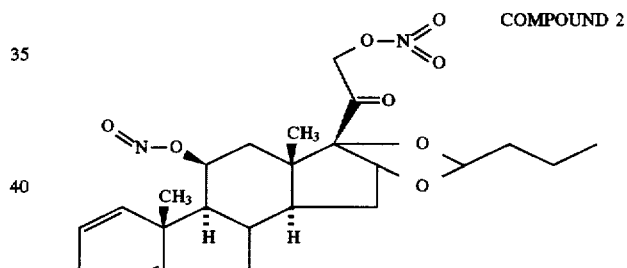

COMPOUND 2

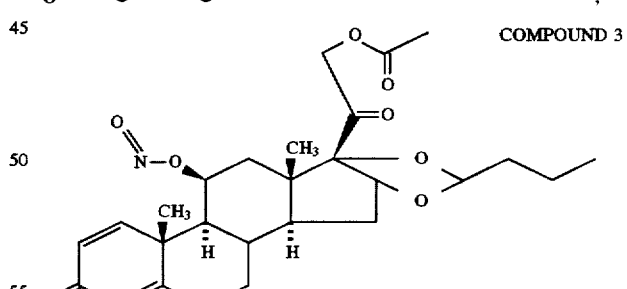

COMPOUND 3

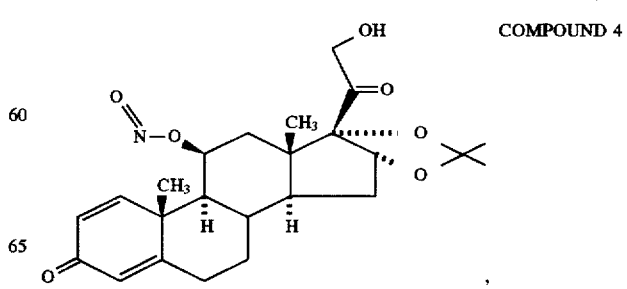

COMPOUND 4

COMPOUND 5
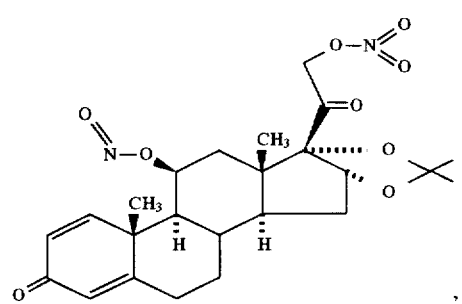
COMPOUND 6
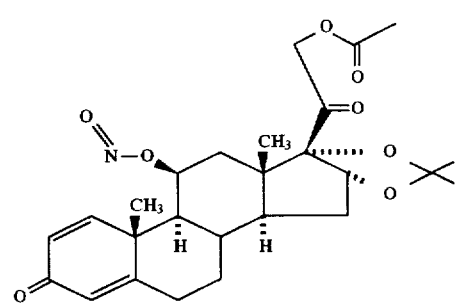
COMPOUND 7
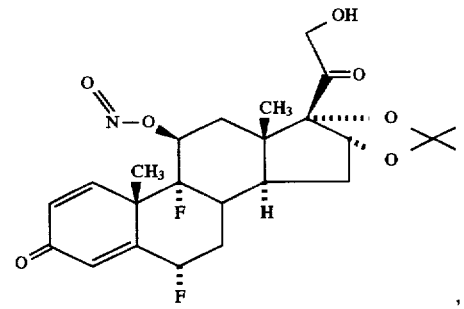
COMPOUND 8
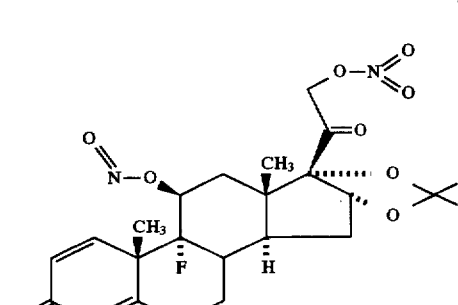
COMPOUND 9
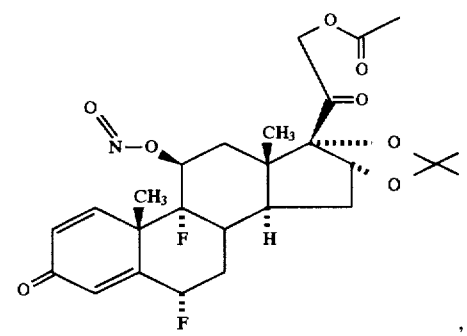
COMPOUND 10
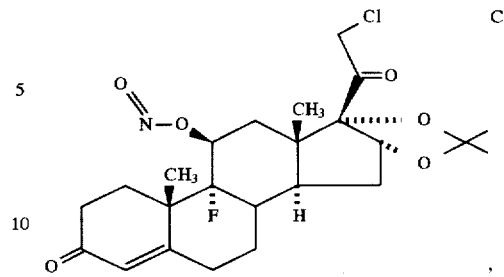
COMPOUND 11
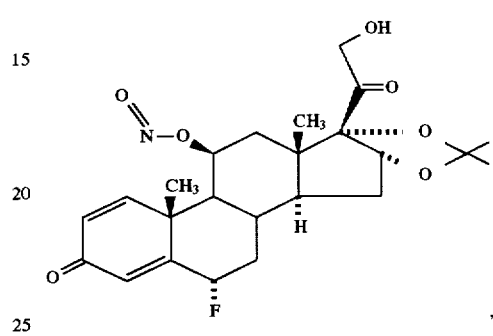
COMPOUND 12
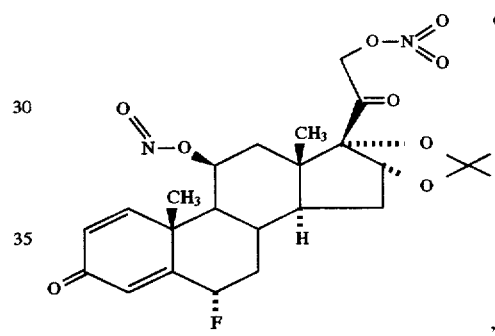
COMPOUND 13
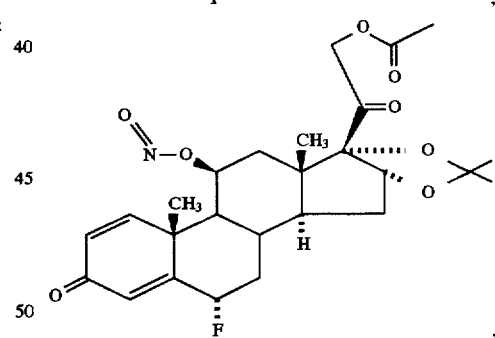
COMPOUND 14
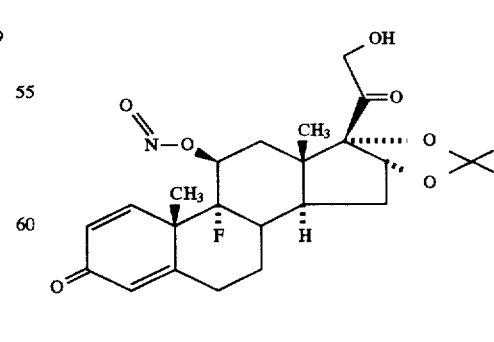

-continued
COMPOUND 15
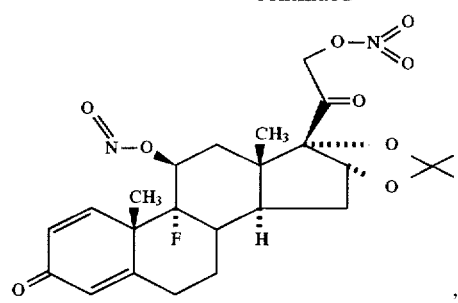
COMPOUND 16
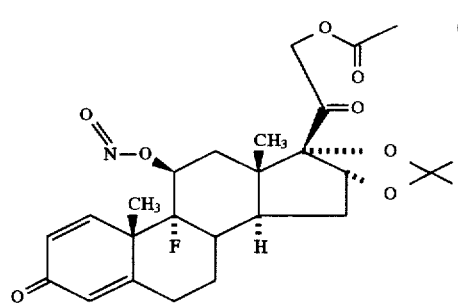
COMPOUND 17
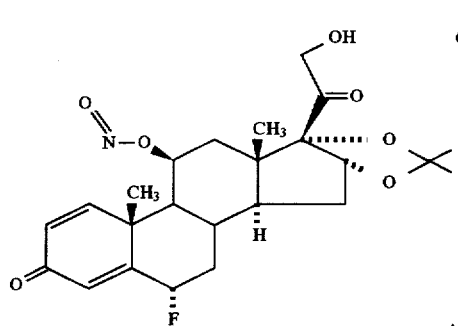
COMPOUND 18
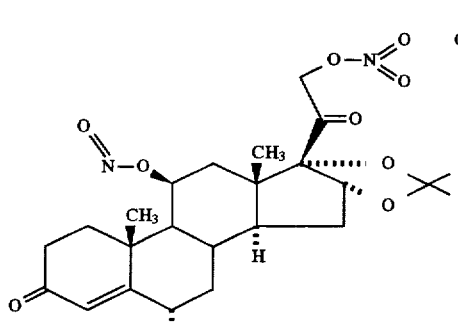
COMPOUND 19
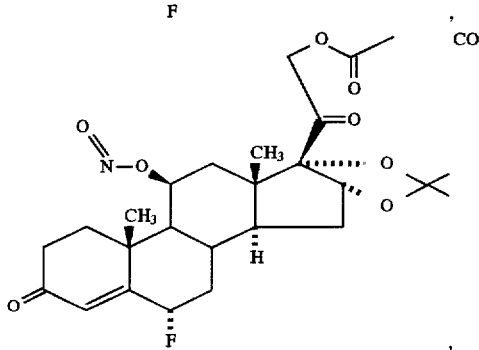
-continued
COMPOUND 20
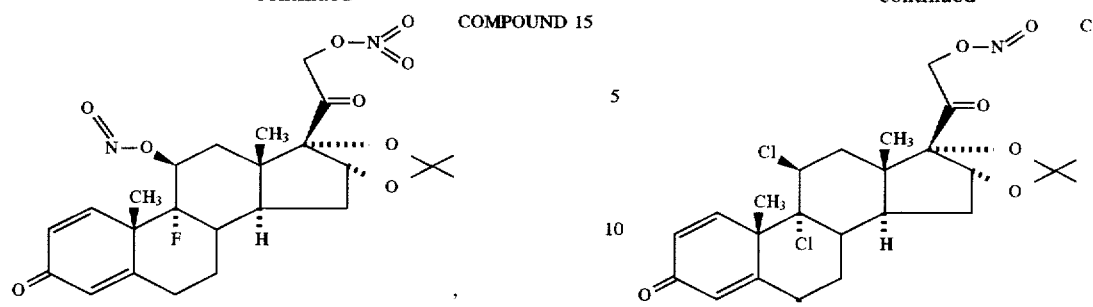
COMPOUND 21
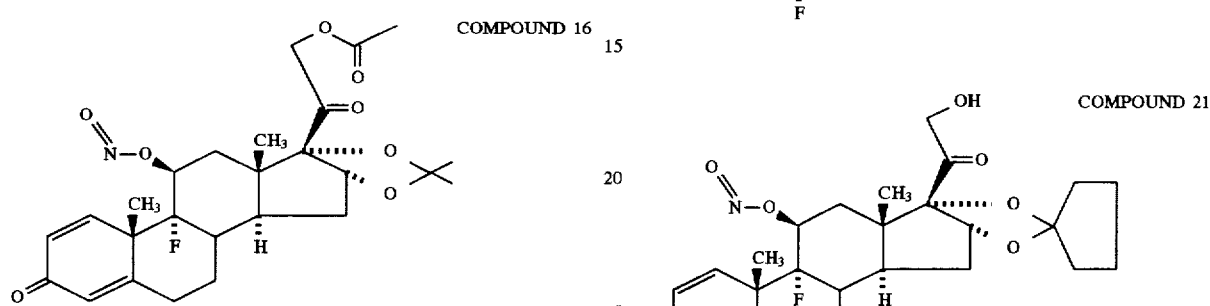
COMPOUND 22
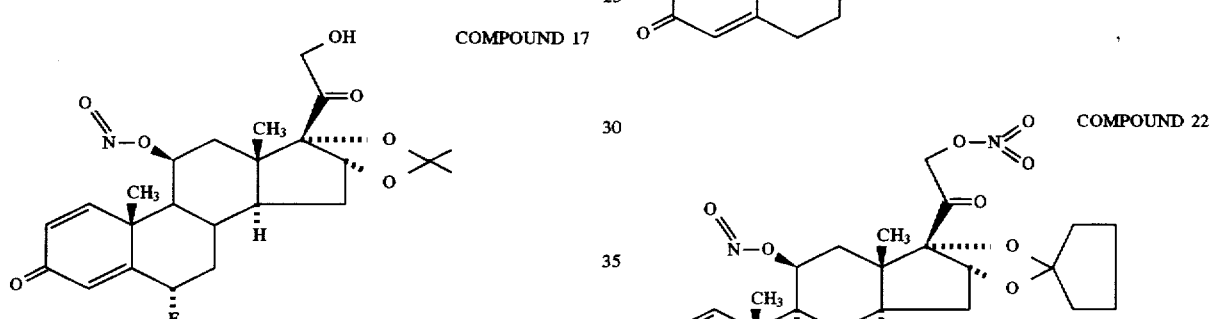
and
COMPOUND 23
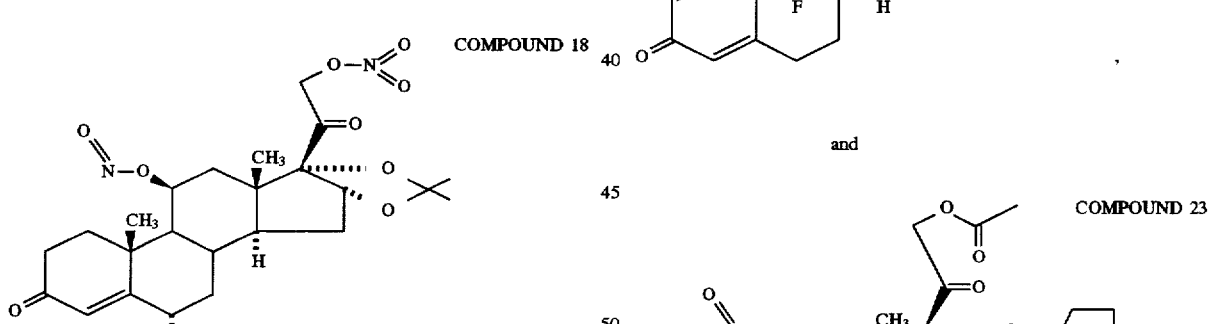
together with a pharmaceutically acceptable carrier.
8. A pharmaceutical composition comprising a compound having the formula:

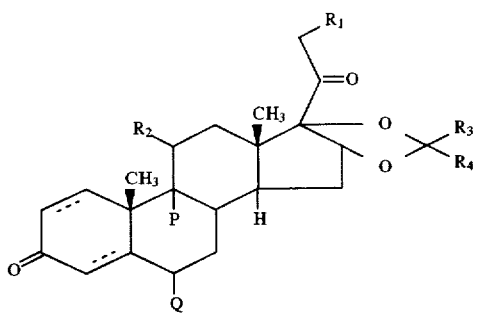

or an ester thereof, wherein:
the dotted line indicates a single or a double bond;
$R_1$ is selected from the group consisting of hydrogen, hydroxy, nitrite ester (ONO), nitrate ester ($ONO_2$), halogen, sulfhydryl, lower thioalkyl, acyloxy, lower alkoxy, alkylsilyloxy, lower alkyl, lower alkenyl, lower alkynyl, alicyclic hydrocarbon and heterocyclic;
$R_2$ selected from the group consisting of hydrogen, hydroxy, nitrite ester (ONO), nitrate ester ($ONO_2$), and acyloxy,
$R_3$ and $R_4$ are independently selected from the group consisting of hydrogen, lower alkyl, lower alkenyl, and lower alkynyl, alicyclic hydrocarbon and heterocyclic;
or $R_3$ and $R_4$ are taken together to form an alicyclic hydrocarbon or heterocyclic ring;
P and Q are independently selected from the group consisting of hydrogen, halogen, lower alkyl, lower alkenyl, and lower alkynyl; and
With the proviso that $R_1$ or $R_2$ or $R_1$ and $R_2$ are nitrite ester (ONO);
together with a pharmaceutically acceptable formulation selected from the group consisting of:
capsules, cachets, tablets, powder, granules, solution or suspension in a non-aqueous liquid, non-aqueous sterile injection solution, suppositories, lozenges, and aerosolized medicaments.

9. The pharmaceutical composition as recited in claim 8 wherein;
the dotted lines indicate a single or a double bond;
$R_1$ is selected from the group consisting of hydrogen, hydroxy, nitrite ester (ONO), nitrate ester ($ONO_2$), halogen, lower thioalkyl group of 1 to 4 carbon atoms, heterocyclic group of 2 to 5 carbon atoms and 1 to 2 hetero atoms, lower alkoxy group of 1 to 6 carbon atoms, alkylsilyloxy group of 3 to 8 carbon atoms, lower alkyl group of 1 to 6 carbon atoms, acyloxy group of 2 to 6 carbon atoms and alicyclic hydrocarbon of 3 to 6 carbon atoms;
$R_2$ is selected from the group consisting of hydrogen, hydroxy, nitrite ester (ONO), nitrate ester ($ONO_2$), and acyloxy group of 2 to 4 carbon atoms;
$R_3$ and $R_4$ are independently selected from the group consisting of hydrogen, lower alkyl of 1 to 8 carbon atoms, alicyclic hydrocarbon of 3 to 6 carbon atoms, and heterocyclic of 2 to 5 carbon atoms and 1 to 2 heteroatoms;
or $R_3$ and $R_4$ are taken together to form an alicyclic of 3 to 8 carbon atoms or heterocyclic ring of 2 to 5 carbon atoms and 1 to 2 hetero atoms;
P and Q are independently selected from the group consisting of hydrogen, chloro, fluoro and lower alkyl group of 1 to 4 carbon atoms; and With the proviso that $R_1$ or $R_2$ or $R_1$ and $R_2$ are nitrite ester (ONO);
together with a pharmaceutically acceptable formulation selected from the group consisting of:
capsules, cachets, tablets, powder, granules, solution or suspension in a non-aqueous liquid, non-aqueous sterile injection solution, suppositories, lozenges, and aerosolized medicaments.

10. The pharmaceutical composition as recited in claim 8 wherein;
the dotted lines indicate a single or a double bond;
$R_1$ is selected from the group consisting of hydrogen, hydroxy, nitrite ester (ONO), nitrate ester ($ONO_2$), halogen, sulfhydryl, lower thioalkyl group of 1 to 4 carbon atoms, heterocyclic group of 2 to 4 carbon atoms and 1 to 2 hetero atoms, lower alkoxy group of 1 to 4 carbon atoms, alkylsilyloxy group of 3 to 4 carbon atoms, lower alkyl group of 3 to 6 carbon atoms, and acyloxy group of 2 to 4 carbon atoms;
$R_2$ is selected from the group consisting of hydroxy, nitrite ester (ONO), nitrate ester ($ONO_2$), and acyloxy group of 2 to 3 carbon atoms;
$R_3$ and $R_4$ are independently selected from the group consisting of hydrogen, and lower alkyl group of 1 to 6 carbon atoms;
or $R_3$ and $R_4$ are taken together to form an alicyclic of 3 to 6 carbon atoms or heterocyclic ring of 3 to 4 carbon atoms and 1 to 2 hetero atoms;
P and Q are independently selected from the group consisting of hydrogen, chloro, fluoro and lower alkyl group of 1 to 3 carbon atoms; and
With the proviso that at least one or both $R_1$ or $R_2$ is nitrite ester (ONO);
together with a pharmaceutically acceptable formulation selected from the group consisting of:
capsules, cachets, tablets, powder, granules, solution or suspension in a non-aqueous liquid, non-aqueous sterile injection solution, suppositories, lozenges, and aerosolized medicaments.

11. The pharmaceutical composition as recited in claim 8 wherein;
the dotted lines indicate a single or a double bond;
$R_1$ is selected from the group consisting of hydroxy, nitrite ester (ONO), nitrate ester ($ONO_2$), and chloro;
$R_2$ is selected from the group consisting of hydroxy, nitrite ester (ONO), and nitrate ester ($ONO_2$);
$R_3$ and $R_4$ are independently selected from the group consisting of hydrogen, methyl, ethyl and propyl;
P and Q are independently selected from a group of hydrogen, chloro, fluoro and methyl; and
With the proviso that $R_1$ or $R_2$ or $R_1$ and $R_2$ are nitrite ester (ONO);
together with a pharmaceutically acceptable formulation selected from the group consisting of:
capsules, cachets, tablets, powder, granules, solution or suspension in a non-aqueous liquid, non-aqueous sterile injection solution, suppositories, lozenges, and aerosolized medicaments.

12. The pharmaceutical composition recited in claim 8 wherein the compound is selected from the following:

COMPOUND 1
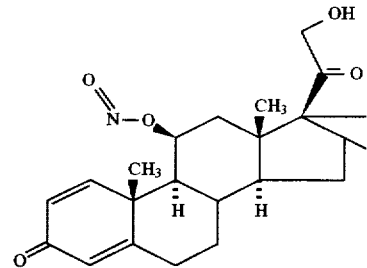
COMPOUND 6
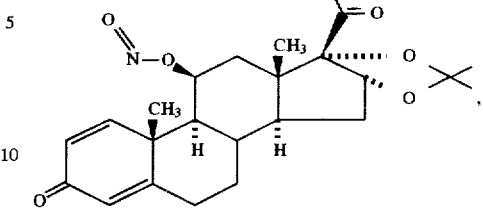
COMPOUND 2
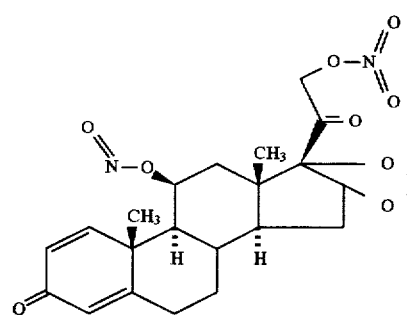
COMPOUND 7
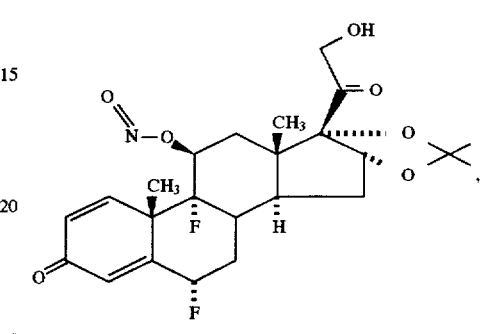
COMPOUND 3
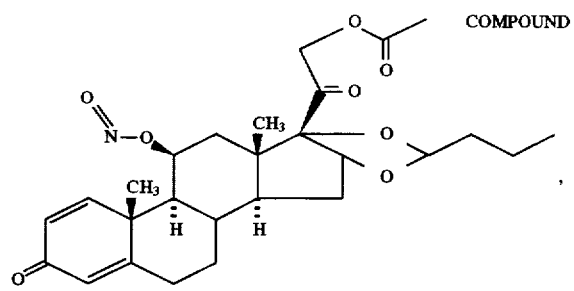
COMPOUND 8
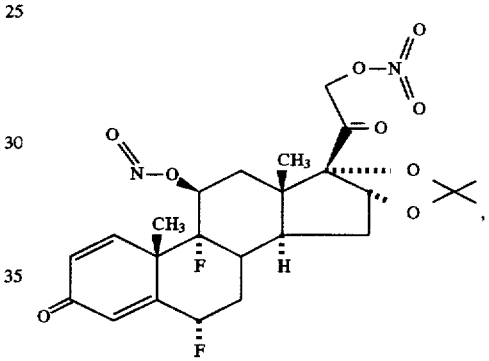
COMPOUND 4
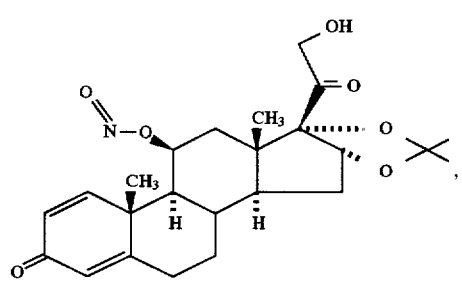
COMPOUND 9
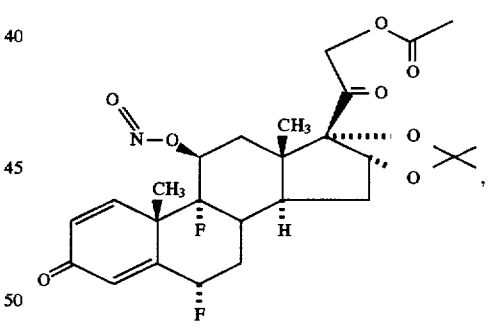
COMPOUND 5
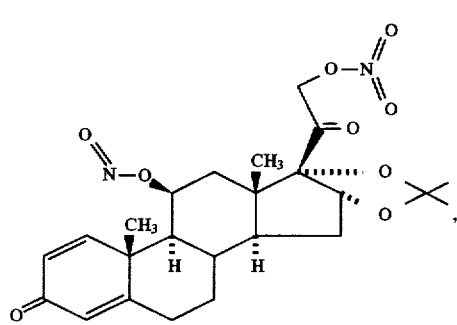
COMPOUND 10
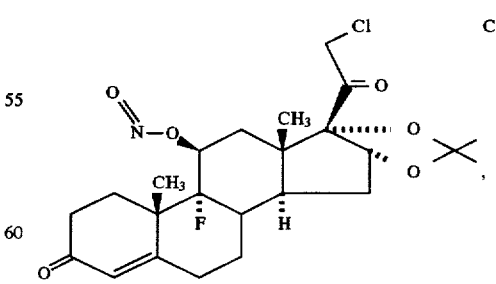

COMPOUND 11
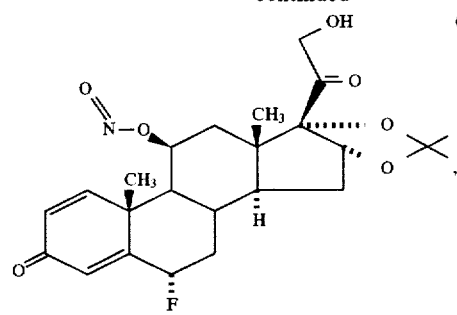
COMPOUND 16
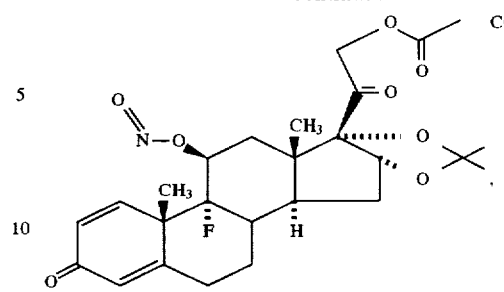
COMPOUND 12
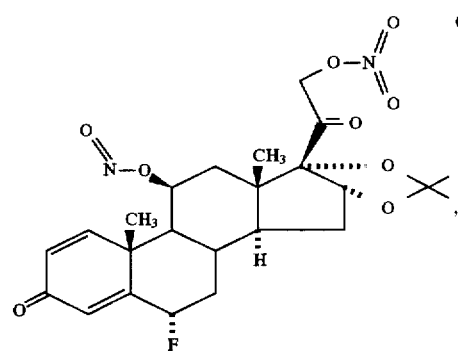
COMPOUND 17
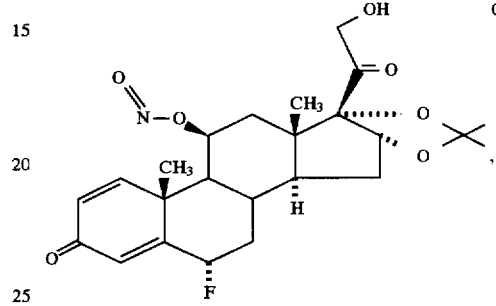
COMPOUND 13
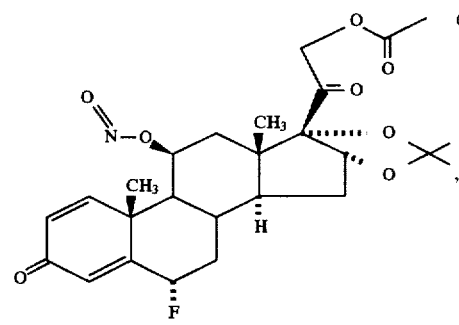
COMPOUND 18
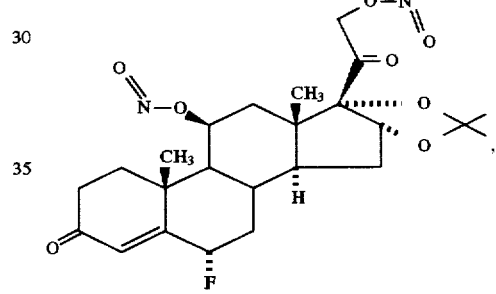
COMPOUND 14
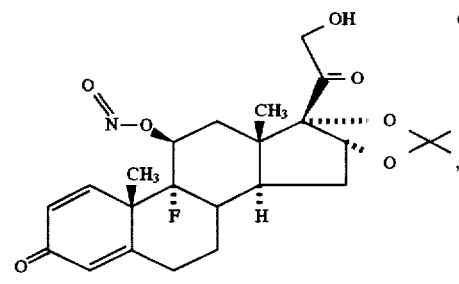
COMPOUND 19
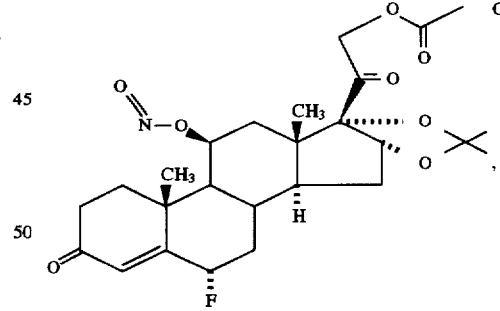
COMPOUND 15
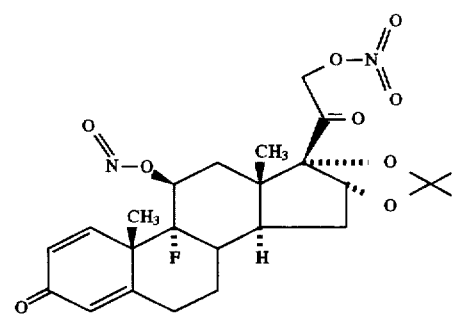
COMPOUND 21
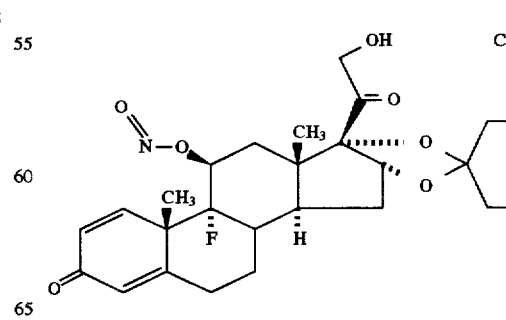

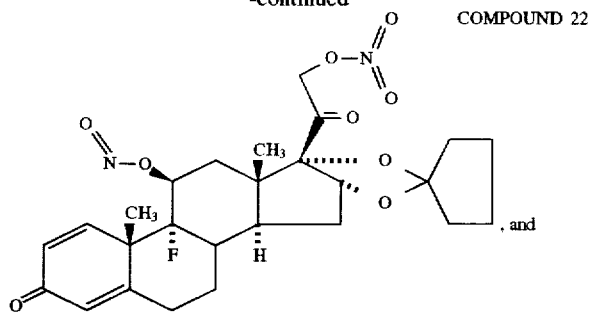

COMPOUND 22

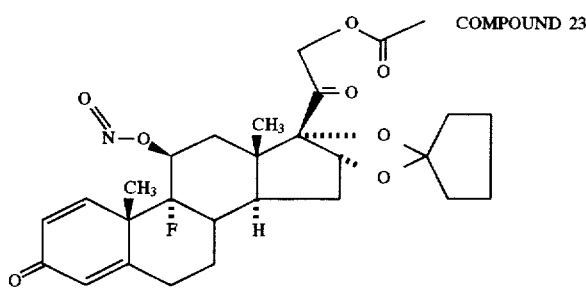

COMPOUND 23 together with a pharmaceutically acceptable formulation selected from the group consisting of:

capsules, cachets, tablets, powder, granules, solution or suspension in a non-aqueous liquid, non-aqueous sterile injection solution, suppositories, lozenges, and aerosolized medicaments.

13. A method of treating a patient with inflammation by administering a therapeutically effective amount of a compound having the formula:

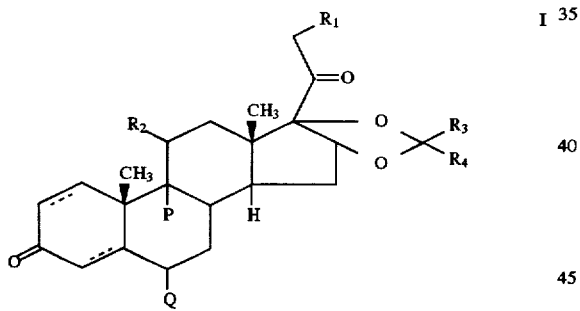

I or an ester thereof, wherein;

the dotted line indicates a single or a double bond;

$R_1$ is selected from the group consisting of hydrogen, hydroxy, nitrite ester (ONO), nitrate ester ($ONO_2$), halogen, sulfhydryl, lower thioalkyl, acyloxy, lower alkoxy, alkylsilyloxy, lower alkyl, lower alkenyl, lower alkynyl, alicyclic hydrocarbon and heterocyclic;

$R_2$ is selected from the group consisting of hydrogen, hydroxy, nitrite ester (ONO), nitrate ester ($ONO_2$), and acyloxy;

$R_3$ and $R_4$ are independently selected from the group consisting of hydrogen, lower alkyl, lower alkenyl, and lower alkynyl, alicyclic hydrocarbon and heterocyclic;

or $R_3$ and $R_4$ are taken together to form an alicyclic hydrocarbon or heterocyclic ring;

P and Q are independently selected from the group consisting of hydrogen, halogen, lower alkyl, lower alkenyl, and lower alkynyl; and With the proviso that $R_1$ or $R_2$ or $R_1$ and $R_2$ are nitrite ester (ONO).

14. The method of treating a patient with inflammation as recited in claim 13 wherein;

the dotted lines indicate a single or a double bond;

$R_1$ is selected from the group consisting of hydrogen, hydroxy, nitrite ester (ONO), nitrate ester ($ONO_2$), halogen, lower thioalkyl group of 1 to 4 carbon atoms, heterocyclic group of 2 to 5 carbon atoms and 1 to 2 hetero atoms, lower alkoxy group of 1 to 6 carbon atoms, alkylsilyloxy group of 3 to 8 carbon atoms, lower alkyl group of 1 to 6 carbon atoms, acyloxy group of 2 to 6 carbon atoms and alicyclic hydrocarbon of 3 to 6 carbon atoms;

$R_2$ is selected from the group consisting of hydrogen, hydroxy, nitrite ester (ONO), nitrate ester ($ONO_2$), and acyloxy group of 2 to 4 carbon atoms;

$R_3$ and $R_4$ are independently selected from the group consisting of hydrogen, lower alkyl of 1 to 8 carbon atoms, alicyclic hydrocarbon of 3 to 6 carbon atoms, and heterocyclic of 2 to 5 carbon atoms and 1 to 2 heteroatoms;

or $R_3$ and $R_4$ are taken together to form an alicyclic of 3 to 8 carbon atoms or heterocyclic ring of 2 to 5 carbon atoms and 1 to 2 hetero atoms;

P and Q are independently selected from the group consisting of hydrogen, chloro, fluoro and lower alkyl group of 1 to 4 carbon atoms; and With the proviso that $R_1$ or $R_2$ or $R_1$ and $R_2$ are nitrite ester (ONO).

15. The method of treating a patient with inflammation as recited in claim 13 wherein;

the dotted lines indicate a single or a double bond;

$R_1$ is selected from the group consisting of hydrogen, hydroxy, nitrite ester (ONO), nitrate ester ($ONO_2$), halogen, sulfhydryl, lower thioalkyl group of 1 to 4 carbon atoms, heterocyclic group of 2 to 4 carbon atoms and 1 to 2 hetero atoms, lower alkoxy group of 1 to 4 carbon atoms, alkylsilyloxy group of 3 to 4 carbon atoms, lower alkyl group of 3 to 6 carbon atoms, and acyloxy group of 2 to 4 carbon atoms;

$R_2$ is selected from the group consisting of hydroxy, nitrite ester (ONO), nitrate ester ($ONO_2$), and acyloxy group of 2 to 3 carbon atoms;

$R_3$ and $R_4$ are independently selected from the group consisting of hydrogen, and lower alkyl group of 1 to 6 carbon atoms;

or $R_3$ and $R_4$ are taken together to form an alicyclic of 3 to 6 carbon atoms or heterocyclic ring of 3 to 4 carbon atoms and 1 to 2 hetero atoms;

P and Q are independently selected from the group consisting of hydrogen, chloro, fluoro and lower alkyl group of 1 to 3 carbon atoms; and With the proviso that at least one or both $R_1$ or $R_2$ is nitrite ester (ONO).

16. The method of treating a patient with inflammation as recited in claim 13 wherein;

the dotted lines indicate a single or a double bond;

$R_1$ is selected from the group consisting of hydroxy, nitrite ester (ONO), nitrate ester ($ONO_2$), and chloro;

$R_2$ is selected from the group consisting of hydroxy, nitrite ester (ONO), and nitrate ester ($ONO_2$);

$R_3$ and $R_4$ are independently selected from the group consisting of hydrogen, methyl, ethyl and propyl;

P and Q are independently selected from a group of hydrogen, chloro, fluoro and methyl; and With the proviso that $R_1$ or $R_2$ or $R_1$ and $R_2$ are nitrite ester (ONO).
17. A method of treating a patient with inflammation as recited in claim 13 wherein the compound is selected from the following:
COMPOUND 1
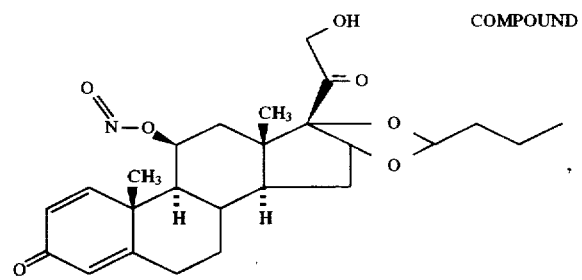
COMPOUND 2
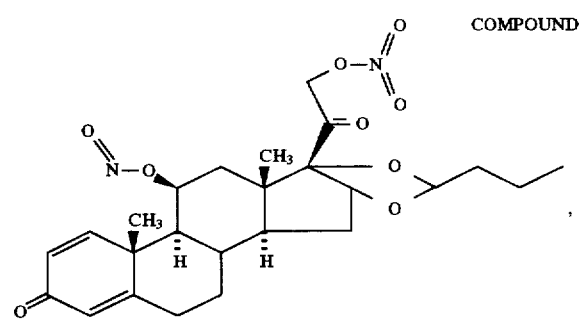
COMPOUND 3
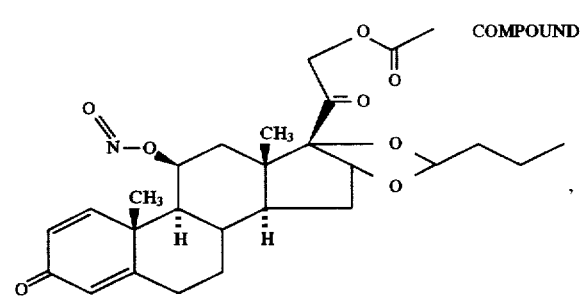
COMPOUND 4
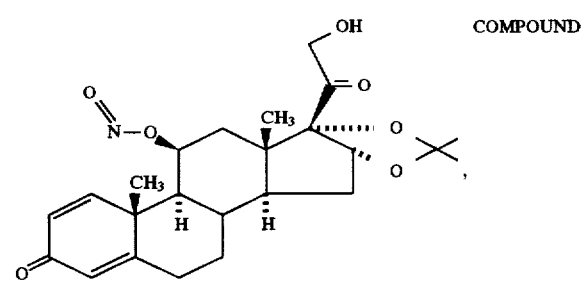
COMPOUND 5
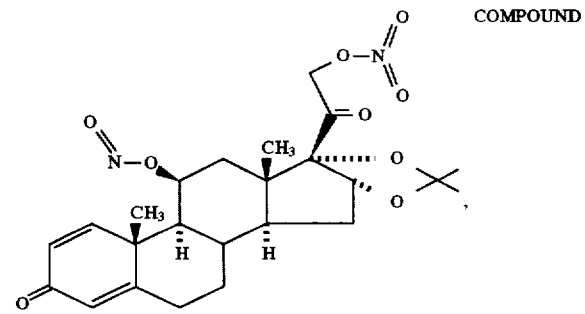
-continued
COMPOUND 6
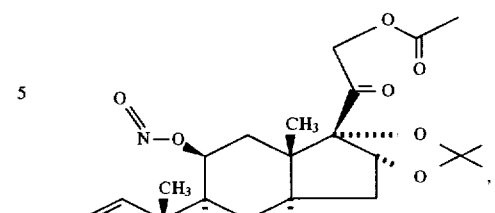
COMPOUND 7
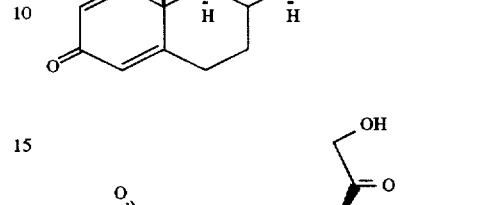
COMPOUND 8
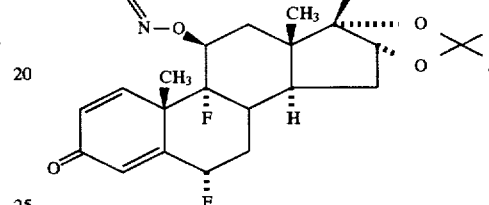
COMPOUND 9
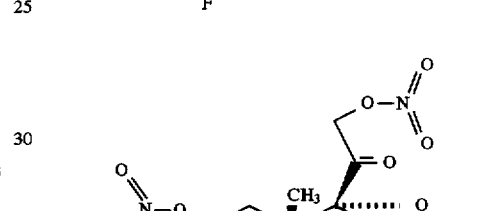
COMPOUND 10
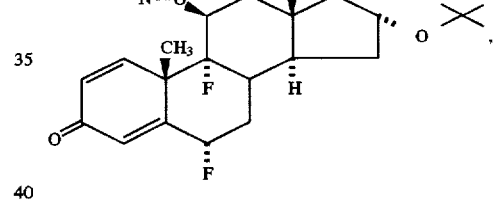

-continued
COMPOUND 11
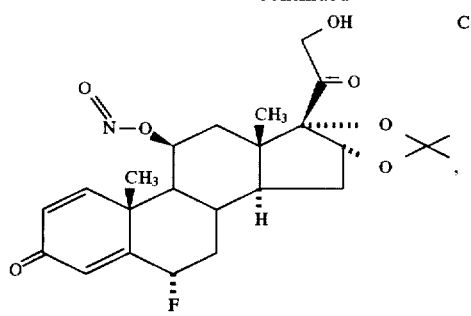
COMPOUND 16
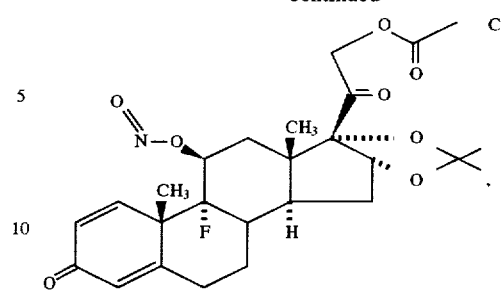
COMPOUND 12
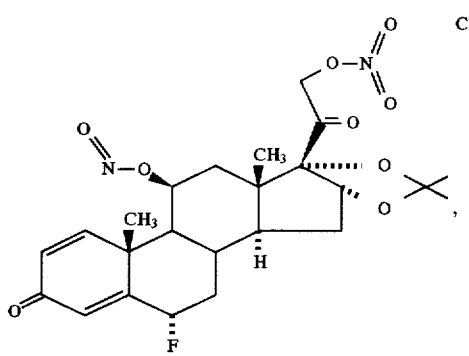
COMPOUND 17
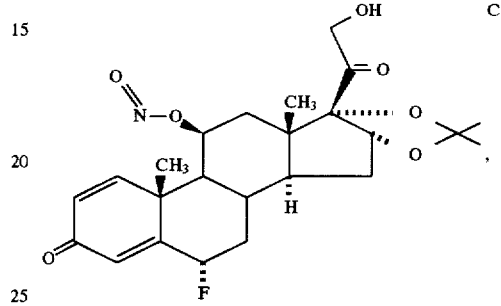
COMPOUND 18
COMPOUND 13
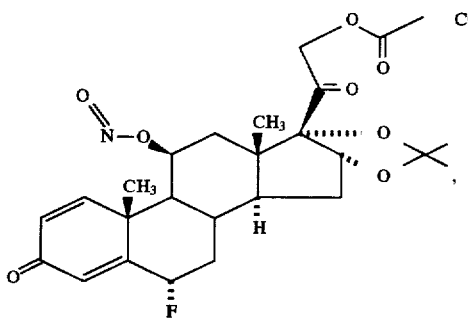
COMPOUND 14
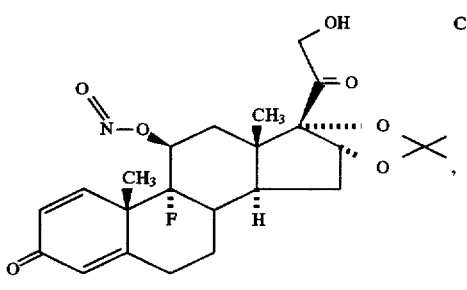
COMPOUND 19
COMPOUND 15
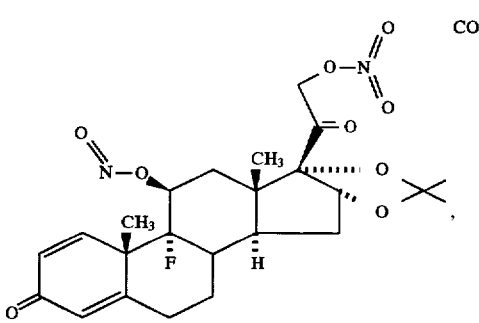
COMPOUND 21
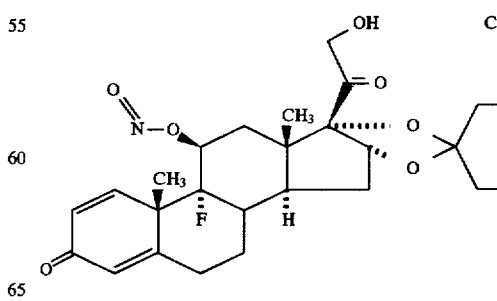

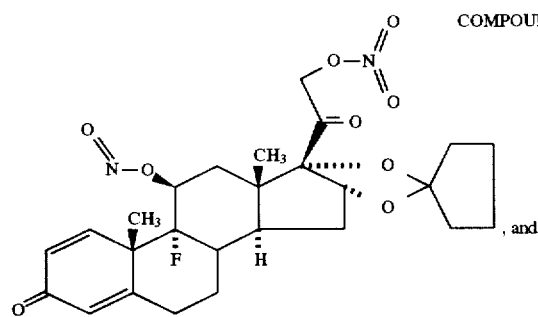
COMPOUND 22
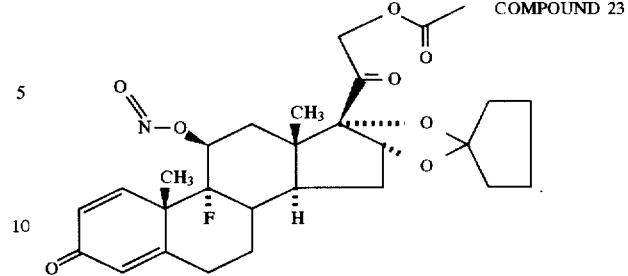
COMPOUND 23
18. The method of claims 13, 14, 15, 16, or 17 wherein said patient also has undesired smooth muscle contractions.
* * * * *